US010730840B2

(12) United States Patent
Redda et al.

(10) Patent No.: US 10,730,840 B2
(45) Date of Patent: Aug. 4, 2020

(54) SUBSTITUTED TETRAHYDROISOQUINOLINE ETHYLBENZAMIDE ANTI-CANCER AGENTS

(71) Applicant: Florida A&M University, Tallahassee, FL (US)

(72) Inventors: Kinfe Ken Redda, Tallahassee, FL (US); Suresh Kumar V. K. Eyunni, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 19 days.

(21) Appl. No.: 16/132,853

(22) Filed: Sep. 17, 2018

(65) Prior Publication Data

US 2019/0100495 A1    Apr. 4, 2019

Related U.S. Application Data

(60) Provisional application No. 62/567,880, filed on Oct. 4, 2017.

(51) Int. Cl.
*C07D 217/08* (2006.01)
*A61P 35/00* (2006.01)
*C07D 405/04* (2006.01)

(52) U.S. Cl.
CPC ............ *C07D 217/08* (2013.01); *A61P 35/00* (2018.01); *C07D 405/04* (2013.01)

(58) Field of Classification Search
CPC ........................... C07D 217/08; C07D 405/04
See application file for complete search history.

(56) References Cited

U.S. PATENT DOCUMENTS 8,889,713 B1 * 11/2014 Redda .................. C07D 417/12
514/310

OTHER PUBLICATIONS

Rebecca L. Siegel, MPH; Kimberly D. Miller, MPH; Ahmedin Jemal, DVM, PhD, Cancer Statistics, 2016, CA Cancer J Clin 2016;66:7-30.
Suresh Kumar V. K. Eyunni, Madhavi Gangapuram, and Kinfe K Redda, In-vitro Antiproliferative Activity of New Tetrahydroisoquinolines (THIQs) on Ishikawa Cells and their 3D Pharmacophore Models, Lett Drug Des Discov. 2014 ; 11(4): 428-436. doi:10.2174/1570180811666131203002502.
Anthony A. Colletta, John R. Benson, and Michael Baum, Alternative mechanisms of action of anti-oestrogens, Breast Cancer Research and Treatment 31: 5-9, 1994.
Anju Butta, Kenneth MacLennan, Kathleen C. Flanders, Nigel P. M. Sacks, Ian Smith, Alan McKinna, Mitchell Dowsett, Lalage M. Wakefield, Michael B. Sporn, Michael Baum, and Anthony A. Colletta, Induction of Transforming Growth Factor β1, in Human Breast Cancer in Vivo following Tamoxifen Treatment, American Association for Cancer Research 52, 4261-4264, Aug. 1, 1992.
Mohamed Khairy, Sherif A. El-Safty and Mohamed Ismael, Mesoporous nanomagnet supercaptors for selective heme-proteins from human cells, Chem. Commun., 2012, 48, 10832-10834.
Paul C. D. Hawkins, A. Geoffrey Skillman, Gregory L. Warren, Benjamin A. Ellingson, and Matthew T. Stahl, Conformer Generation with OMEGA: Algorithm and Validation Using High Quality Structures from the Protein Databank and Cambridge Structural Database, J. Chem. Inf. Model. 2010, 50, 572-584.
Gregor Jug, Marko Anderluh and Tihomir Tomašič, Comparative evaluation of several docking tools for docking small molecule ligands to DC-SIGN, J Mol Model (2015) 21: 164, DOI 10.1007/s00894-015-2713-2.
Mark McGann, Anthony Nicholls, Istvan Enyedy, The statistics of virtual screening and lead optimization, J Comput Aided Mol Des (2015) 29:923-936, DOI 10.1007/s10822-015-9861-4.
Mark R. McGann, Harold R. Almond, Anthony Nicholls, J. Andrew Grant, Frank K. Brown, Gaussian Docking Functions, Biopolymers, vol. 68, 76-90 (2003).
C. Kent Osborne, Rachel Schiff, Grazia Arpino, Adrian Susan Lee, V.G. Hilsenbeck, Endocrine responsiveness: Understanding how progesterone receptor can be used to select endocrine therapy, The Breast (2005) 14, 458-465.
Philipp Y. Maximov, Theresa M. Lee and V. Craig Jordan, The Discovery and Development of Selective Estrogen Receptor Modulators (SERMs) for Clinical Practice, Current Clinical Pharmacology, 2013, 8, 135-155.
M. Clarke, R. Collins, C. Davies, J. Godwin, R. Gray, and R. Peto, Tamoxifen for early breast cancer: an overview of the randomised trials, The Lancet • vol. 351 • May 16, 1998.
Leonard J. Lerner and V. Craig Jordan, Development of Antiestrogens and Their Use in Breast Cancer: Eighth Cain Memorial Award Lecture, American Association for Cancer Research 50, 4177-4189. Jul. 15, 1990.
Jonna Frasor, Fabio Stossi, Jeanne M. Danes, Barry Komm, C. Richard Lyttle, and Benita S. Katzenellenbogen, Selective Estrogen Receptor Modulators: Discrimination of Agonistic versus Antagonistic Activities by Gene Expression Profiling in Breast Cancer Cells, American Association for Cancer Research 64, 1522-1533, Feb. 15, 2004.
CK Osborne, A Wakeling and RI Nicholson, Fulvestrant: an oestrogen receptor antagonist with a novel mechanism of action, British Journal of Cancer (2004) 90(Suppl 1), S2-S6.

(Continued)

*Primary Examiner* — Joseph R Kosack
(74) *Attorney, Agent, or Firm* — Thomas | Horstemeyer, LLP

(57) ABSTRACT

The compounds herein disclosed are N-substituted tetrahydroisoquinoline ethylbenzamide compounds that have modifications on the phenyl rings by introducing groups with various electronic properties. These derivatives of N-substituted tetrahydroisoquinoline ethylbenzamide compounds have been shown to have anti-proliferative activity against cells. In particular, the compounds have been found to be effective in inhibiting the proliferation of cancer cells, such as cancer cells that originated in breast tissue. Additionally, it has been shown that the novel compounds have $IC_{50}$ values against the breast cancer cells that are 6- to 10-fold less than the $IC_{50}$ of Tamoxifen.

23 Claims, 17 Drawing Sheets

(56) References Cited

OTHER PUBLICATIONS

Meihua Sui, Yi Huang, Ben Ho Park, Nancy E. Davidson, and Weimin Fan, Estrogen Receptor α Mediates Breast Cancer Cell Resistance to Paclitaxel through Inhibition of Apoptotic Cell Death, Cancer Res 2007; 67: (11). Jun. 1, 2007.

Hani El Amouri, Anne Vessiéres, Dominique Vichard, Siden Top, Michel Gruselle, and Gérard Jaouen, Syntheses and Affinities of Novel Organometallic-Labeled Estradiol Derivatives: A Structure-Affinity Relationship, J. Med. Chem. 1992, 35, 3130-3135.

Naseem Ahmed, Celena Dubuc, Jacques Rousseau, Francois Be'nard and Johan E. van Lier, Synthesis, characterization, and estrogen receptor binding affinity of flavone-, indole-, and furan-estradiol conjugates, Bioorganic & Medicinal Chemistry Letters 17 (2007) 3212-3216.

V. Craig Jordan, Chemoprevention of breast cancer with selective oestrogen-receptor modulators, Nature Reviews | Cancer Jan. 2007 | vol. 7.

George G. J. M. Kuiper, Bo Carlsson, Kaj Grandien, Eva Enmark, Johan Haggblad, Stefan Nilsson, and Jan-Åke Gustafsson, Comparison of the Ligand Binding Specificity and Transcript Tissue Distribution of Estrogen Receptors α and β.

H. Seeger, J. Huober, D. Wallwiener, A.O. Mueck, Inhibition of Human Breast Cancer Cell Proliferation with Estradiol Metabolites is as Effective as with Tamoxifen, Horm Metab Res 2004; 36: 277-280.

Bernard Fisher, Joseph P. Costantino, D. Lawrence Wickerham, Carol K. Redmond, Maureen Kavanah, Walter M. Cronin, Victor Vogel, Andre'Robidoux, Nikolay Dimitrov, James Atkins, Mary Daly, Samuel Wieand, Elizabeth Tan-Chiu, Leslie Ford, Norman Wolmark, and other National Surgical Adjuvant Breast and Bowel Project Investigators, Tamoxifen for Prevention of Breast Cancer: Report of the National Surgical Adjuvant Breast and Bowel Project P-1 Study, Journal of the National Cancer Institute, vol. 90, No. 18, Sep. 16, 1998.

Phillips & Venitt (1993) Lancet 341: 1485-1486.

V. Craig Jordan, Tamoxifen: A Most Unlikely Pioneering Medicine, Nature Reviews | Drug Discovery vol. 2 | March 2003 | 207.

Johanne Renaud, Serge Francüois Bischoff, Thomas Buhl, Philipp Floersheim, Brigitte Fournier, Christine Halleux, Joerg Kallen, Hansjoerg Keller, Jean-Marc Schlaeppi, and Wilhelm Stark, Estrogen Receptor Modulators: Identification and Structure-Activity Relationships of Potent ERα-Selective Tetrahydroisoquinoline Ligands, J. Med. Chem. 2003, 46, 2945-2957.

Hsiang-Ru Lin, Martin K. Safo and Donald J. Abraham, Identification of a series of tetrahydroisoquinoline derivatives as potential therapeutic agents for breast cancer, H.-R. Lin et al. / Bioorg. Med. Chem. Lett. 17 (2007) 2581-2589.

Johanne Renaud, Serge Francüois Bischoff, Thomas Buhl, Philipp Floersheim, Brigitte Fournier, Martin Geiser, Christine Halleux, Joerg Kallen, Hansjoerg Keller, and Paul Ramage, Selective Estrogen Receptor Modulators with Conformationally Restricted Side Chains. Synthesis and Structure-Activity Relationship of ERr-Selective Tetrahydroisoquinoline Ligands, J. Med. Chem. 2005, 48, 364-379.

Harika Atmaca, Selim Uzunoglu, Anti-angiogenic effects of trabectedin (Yondelis; ET-743) on human breast cancer cells, Eur. Cytokine Netw. vol. 25 n° 1, Mar. 2014, 1-7.

Pranesh Kumar, Atul Rawat, Amit K. Keshari, Ashok K. Singh, Siddhartha Maity, Arnab De, Amalesh Samanta & Sudipta Saha, Antiproliferative effect of isolated isoquinoline alkaloid from Mucuna pruriens seeds in hepatic carcinoma cells, Natural Product Research, 2016 vol. 30, No. 4, 460-463.

Jonathan W. Lane, Alberto Estevez, Kyle Mortara, Ondine Callan, Jeffrey R. Spencer and Robert M. Williams, Antitumor activity of tetrahydroisoquinoline analogues 3-epi-jorumycin and 3-epi-renieramycin G, J. W. Lane et al. / Bioorg. Med. Chem. Lett. 16 (2006) 3180-3183.

Eda Acikgoz, Ummu Guven, Fahriye Duzagac, Ruchan Uslu, Mikail Kara, Burak, Cem Soner, Gulperi Oktem, Enhanced G2/M Arrest, Caspase Related Apoptosis and Reduced E-Cadherin Dependent Intercellular Adhesion by Trabectedin in Prostate Cancer Stem Cells, PLOS ONE | DOI:10.1371/journal.pone.0141090 Oct. 20, 2015.

Mathew P. Leese, Fabrice Jourdan, Wolfgang Dohle, Meriel R. Kimberley, Mark P. Thomas, Ruoli Bai, Ernest Hamel, Eric Ferrandis, and Barry V. L. Potter, Steroidomimetic Tetrahydroisoquinolines for the Design of New Microtubule Disruptors, dx.doi.org/10.1021/ml200232c |ACS Med. Chem. Lett. 2012, 3, 5-9.

Madhavi Gangapuram, Riccardo Jean, Elizabeth Mazzio, Ramesh Badisa, Suresh Eyunni, Carl B. Goodman, Kinfe K. Redda, and Karam F. Soliman, Substituted Tetrahydroisoquinolines as Microtubule-destabilizing Agents in Triple negative Human Breast Cancer Cells, Anticancer Res. Oct. 2016 ; 36(10): 5043-5052.

Madhavi Gangapuram, Suresh Eyunni, and Kinfe K Redda, Synthesis and Pharmacological Evolution of Tetrahydroisoquinolines as Anti Breast Cancer Agents, J Cancer Sci Ther. ; 6: 161-169 doi:10.4172/1948-5956.1000266.

Claude Legault and Andre'B. Charette, Highly Efficient Synthesis of O-(2,4-Dinitrophenyl)hydroxylamine. Application to the Synthesis of Substituted N-Benzoyliminopyridinium Ylides, J. Org. Chem. 2003, 68, 7119-7122 7119.

* cited by examiner

Prior Art Structures

Raloxifen

Doxorubicin

Gemcitabine

Mitoxantrone

Tamoxifen

Reaction Conditons: (i) NaNO₂, CH₃COOH H₂O 0 °C, (ii) Zn, CH₃COOH (iii) 4-Ethylbenzoyl chloride, Et₃N, THF

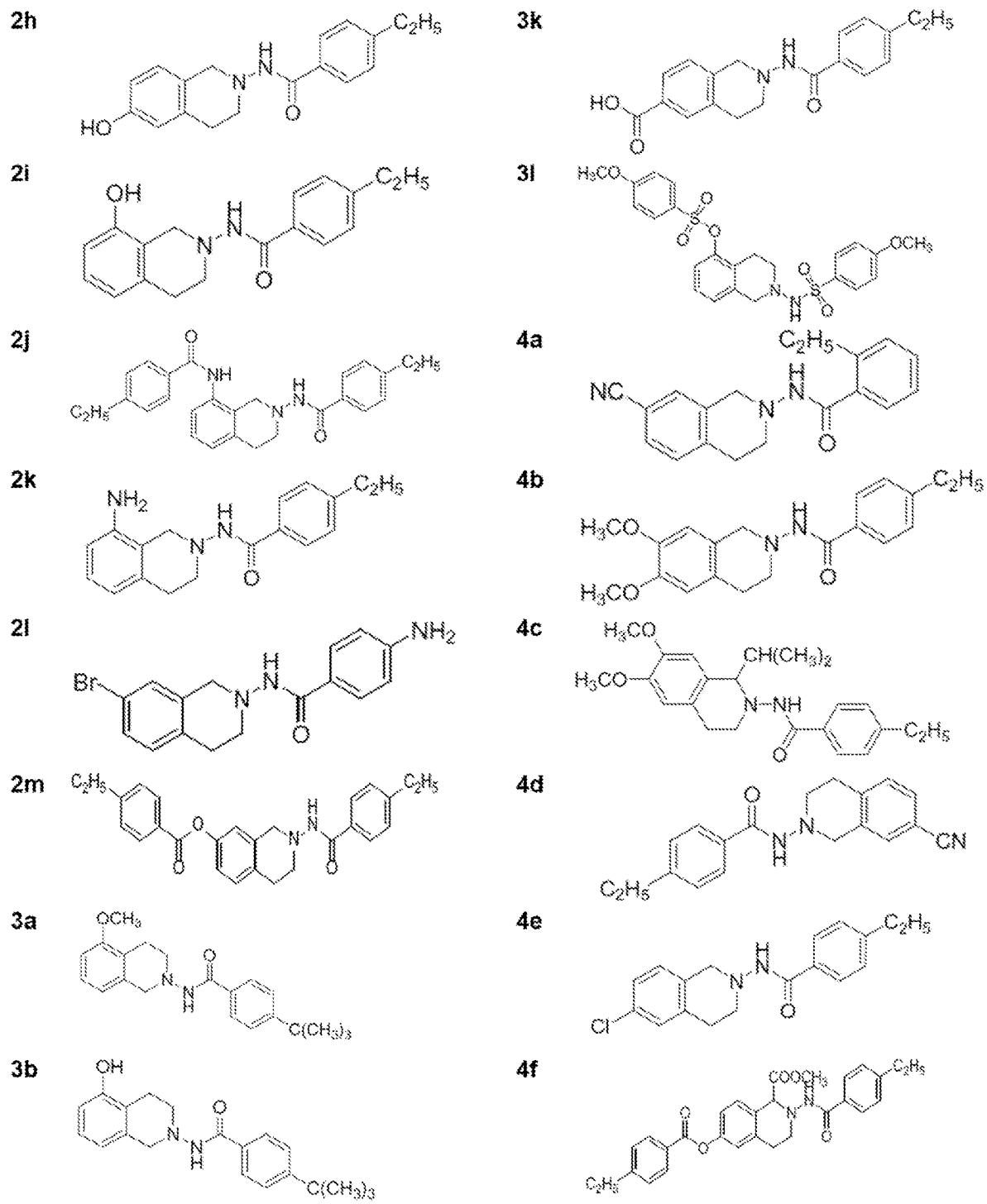
Fig. 17-cont'd

SUBSTITUTED TETRAHYDROISOQUINOLINE ETHYLBENZAMIDE ANTI-CANCER AGENTS

CROSS REFERENCE TO RELATED APPLICATIONS

This application claims priority to and the benefit of U.S. Provisional Patent Application Ser. No. 62/567,880 filed on Oct. 4, 2017 and titled "SUBSTITUTED TETRAHYDROISOQUINOLINE ETHYLBENZAMIDE ANTI-CANCER AGENTS", which is herein incorporated by reference in its entirety.

STATEMENT REGARDING FEDERALLY SPONSORED RESEARCH OR DEVELOPMENT

This invention was made with government support under Grant Nos. G12mD007582-28 and 1P20 MD006738-01 awarded by the National Institutes of Health. The government has certain rights in the invention.

TECHNICAL FIELD

The present disclosure is generally related to substituted tetrahydroisoquinoline ethylbenzamide anti-cancer agents. The present disclosure is also generally related to therapeutic compositions comprising substituted tetrahydroisoquinoline ethylbenzamides and their use as anti-cancer agents.

BACKGROUND

Cancer is considered to be a complex disease state often involving multiple mechanisms through which growth of the cells of a particular organ or tissue in the body go beyond control. Usually, cancer and cancer cells take their name according to the tissue in which the disease originates. Breast cancer is the leading cause of mortality among women resulting in more than half a million deaths worldwide every year. It is the second leading cause of cancer-related deaths in women today and is the most common cancer among women excluding non-melanoma skin cancers. An estimated 252,710 new cases of invasive breast cancer were expected to be diagnosed in women in the U.S alone, along with 63,410 new cases of non-invasive (in situ) breast cancer in the year 2017 (Siegel et al., (2017). *Cancer Stats* 67: 7-30). In 2017, approximately 40,610 women were expected to die from breast cancer. Estrogen receptor (ER), Progesterone receptor (PR) and their associated steroid hormones, play important roles in the development, differentiation, function and growth of normal breast and endometrial cells. ERs are attractive targets in the treatment of breast cancer as they are over-expressed in breast cancer cells. Certain molecules that are selective, non-steroidal and anti-estrogenic products, commonly called Selective Estrogen Receptor Modulators (SERMs) serve as potential alternatives in the treatment of hormone-dependent ER(+) breast cancer (Maximov et al., (2013) *Curr. Clin. Pharmacol.* 8:135-155; Jordan V C. (2007) *Nat. Revs. Cancer* 7: 46-53).

Tetrahydroisoquinoline natural products have shown to exhibit important biological activities that make them essential targets for drug discovery. The tetrahydroisoquinoline family of alkaloids includes potent cytotoxic agents that display a range of biological properties such as antitumor and antimicrobial activities. They were studied thoroughly over a period of more than 40 years, starting with the isolation of naphthyndinomycin in 1974 (Buckingham J B. (1996) *Dictionary of Natural Products*. Vol. 9. Chapman and Hall; USA). 1-Methyl-I, 2, 3, 4-tetrahydraisoquinoline (1-MeTIQ) is considered to be a possible endogenous Parkinsonism-preventing agent and a neuro-protectant. Its ability to antagonize the behavioral syndrome produced by well-known neurotoxins is well documented (Ohta et al., (1990) *Basic, Clinical and Therapeutical Aspects of Alzheimer's and Parkinson's Diseases*, Vol. 1. Plenum Press, N. York).

SUMMARY

One aspect of the disclosure encompasses embodiments of a substituted tetrahydroisoquinoline ethylbenzamide having the formula I:

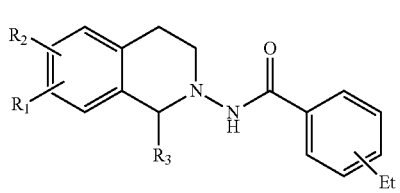

wherein: $R_1$ and $R_2$ can be each independently a hydrogen, a halogen, a methoxy, hydroxyl, cyano, an acyl, a sulfamate, an ethylbenzamide group, an ethylbenzoate group, or an acetamido group; $R_3$ can be hydrogen or a furyl group, wherein when $R_3$ is a furyl group, $R_1$ and $R_2$ are each a hydrogen.

In some embodiments of this aspect of the disclosure, when $R_1$ and $R_3$ are each hydrogen, $R_2$ can be a halogen, a cyano, or a sulfamate.

In some embodiments of this aspect of the disclosure, $R_2$ can be chlorine.

In some embodiments of this aspect of the disclosure, the substituted tetrahydroisoquinoline ethylbenzamide can be selected from the group consisting of N-(7-hydroxy-3,4-dihydroisoquinolin-2(1H)-yl)-4-methoxybenzamide (2d), N-(7-hydroxy-3,4-dihydroisoquinolin-2(1H)-yl)-3-methoxybenzamide (2e), N-(7-hydroxy-3,4-dihydroisoquinolin-2 (1H)-yl)-2-methoxybenzamide (2f), 4-Ethyl-N-(6-hydroxy-3,4-dihydroisoquinolin-2(1H)-yl) benzamide (2h), 4-Ethyl-N-(8-hydroxy-3,4-dihydroisoquinolin-2(1H)-yl) benzamide (2i), N,N'-(3,4-dihydroisoquinoline-2,8(1H)-diyl)bis(4-ethylbenzamide) (2j), N-(8-amino-3,4-dihydroisoquinolin-2 (1H)-yl)-4-ethylbenzamide (2k), 4-Amino-N-(7-bromo-3,4-dihydroisoquinolin-2(1H)-yl) benzamide (2l), 4-(Ethylbenzamido)-1,2,3,4-tetrahydroisoquinolin-7-yl 4-ethylbenzoate (2m), 4-(tert-butyl)-N-(5-Methoxy-3,4-dihydroisoquinolin-2(1H)-yl) benzamide (3a), 4-(tert-butyl)-N-(5-Hydroxy-3,4-dihydroisoquinolin-2(1H)-yl) benzamide (3b), N,N'-(3,4-Dihydroisoquinoline-2,5(1H)-diyl)bis(4-ethylbenzamide) (3c), N-(5-Acetamido-3,4-dihydroisoquinolin-2 (1H)-yl)-4-ethylbenzamide (3d), N-(5-(Benzyloxy)-3,4-dihydroisoquinolin-2(1H)-yl)-4-(tertbutyl) benzamide (3e), 4-Ethyl-N-(5-hydroxy-3,4-dihydroisoquinolin-2(1H)-yl) benzamide (3f), methyl-2-(4-ethylbenzamido)-1,2,3,4-tetrahydroisoquinoline-6-carboxylate (3h), 2-(4-Ethylbenzamido)-1,2,3,4-tetrahydroisoquinoline-6-carboxylic acid (3k), 2-(4-Methoxyphenylsulfonamido)-1,2,3,4-tetrahydroisoquinolin-5-yl-4-methoxybenzene-sulfonate (3l), N-(7-Cyano-3, 4-dihydroisoquinolin-2(1H)-yl)-2-ethylbenzamide (4a), N-(6,7-Dimethoxy-3,4-dihydroisoquinolin-2(1H)-yl)-4-ethylbenzamide (4b), 4-Ethyl-N-(1-isopropyl-6,7-dimethoxy-3,4-dihydroisoquinolin-2(1H)-yl)benzamide (4c), N-(7-Cyano-3,4-dihydroisoquinolin-2(1H)-yl)-4-ethylbenzamide (4d), N-(6-Chloro-3,4-dihydroisoquinolin-2(1H)-yl)-4-ethylbenzamide (4e), methyl-2-(4-ethylbenzamido)-6-((4-ethylbenzoyl)oxy)-1,2,3,4-tetrahydroisoquinoline-1-carboxylate (4f), and N-(7-Chloro-3,4-dihydroisoquinolin-2(1H)-yl)-4-ethylbenzamide (Redda-EVK-I-132).

In some embodiments of this aspect of the disclosure, the substituted tetrahydroisoquinoline ethylbenzamide can be selected from the group consisting of:

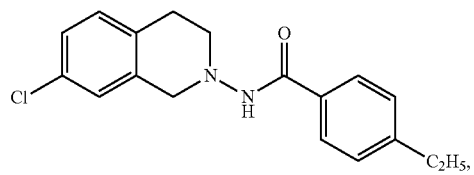

Redda-EVK-I-132

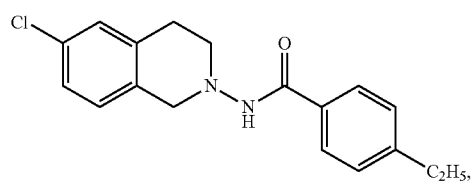

4e

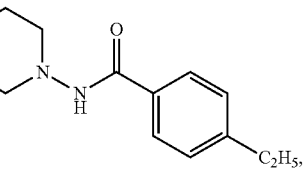

4d

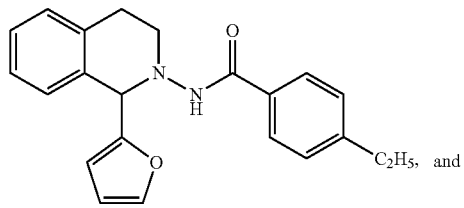

Redda-EVK-I-135

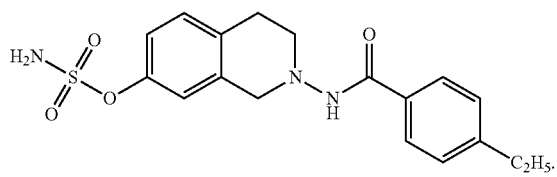

Redda-GM-4-171

In some embodiments of this aspect of the disclosure, the substituted tetrahydroisoquinoline ethylbenzamide has the formula:

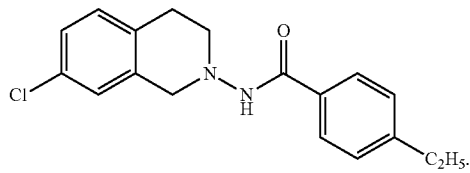

Redda-EVK-I-132

Another aspect of the disclosure encompasses embodiments of a pharmaceutically acceptable composition comprising a substituted tetrahydroisoquinoline ethylbenzamide having the formula I:

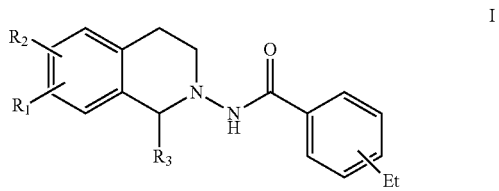

I wherein: $R_1$ and $R_2$ can be each independently a hydrogen, a halogen, a methoxy, hydroxyl, cyano, an acyl, a sulfamate, an ethylbenzamide group, an ethylbenzoate group, or an acetamido group; $R_3$ can be hydrogen or a furyl group, wherein when $R_3$ is a furyl group, $R_1$ and $R_2$ are each a hydrogen; and a pharmaceutically acceptable carrier.

In some embodiments of this aspect of the disclosure, $R_1$ and $R_3$ are each hydrogen, $R_2$ can be a halogen, a cyano, or a sulfamate In some embodiments of this aspect of the disclosure, $R_2$ is chlorine.

In some embodiments of this aspect of the disclosure, the substituted tetrahydroisoquinoline ethylbenzamide can be selected from the group consisting of N-(7-hydroxy-3,4-dihydroisoquinolin-2(1H)-yl)-4-methoxybenzamide (2d), N-(7-hydroxy-3,4-dihydroisoquinolin-2(1H)-yl)-3-methoxybenzamide (2e), N-(7-hydroxy-3,4-dihydroisoquinolin-2(1H)-yl)-2-methoxybenzamide (2f), 4-Ethyl-N-(6-hydroxy-3,4-dihydroisoquinolin-2(1H)-yl) benzamide (2h), 4-Ethyl-N-(8-hydroxy-3,4-dihydroisoquinolin-2(1H)-yl) benzamide (2i), N,N'-(3,4-dihydroisoquinoline-2,8(1H)-diyl)bis(4-ethylbenzamide) (2j), N-(8-amino-3,4-dihydroisoquinolin-2(1H)-yl)-4-ethylbenzamide (2k), 4-Amino-N-(7-bromo-3,4-dihydroisoquinolin-2(1H)-yl) benzamide (2l), 4-(Ethylbenzamido)-1,2,3,4-tetrahydroisoquinolin-7-yl 4-ethylbenzoate (2m), 4-(tert-butyl)-N-(5-Methoxy-3,4-dihydroisoquinolin-2(1H)-yl) benzamide (3a), 4-(tert-butyl)-N-(5-Hydroxy-3,4-dihydroisoquinolin-2(1H)-yl) benzamide (3b), N,N'-(3,4-Dihydroisoquinoline-2,5(1H)-diyl)bis(4-ethylbenzamide) (3c), N-(5-Acetamido-3,4-dihydroisoquinolin-2(1H)-yl)-4-ethylbenzamide (3d), N-(5-(Benzyloxy)-3,4-dihydroisoquinolin-2(1H)-yl)-4-(tertbutyl) benzamide (3e), 4-Ethyl-N-(5-hydroxy-3,4-dihydroisoquinolin-2(1H)-yl) benzamide (3f), methyl-2-(4-ethylbenzamido)-1,2,3,4-tetrahydroisoquinoline-6-carboxylate (3h), 2-(4-Ethylbenzamido)-1,2,3,4-tetrahydroisoquinoline-6-carboxylic acid (3k), 2-(4-Methoxyphenylsulfonamido)-1,2,3,4-tetrahydroisoquinolin-5-yl-4-methoxybenzene-sulfonate (3l), N-(7-Cyano-3,4-dihydroisoquinolin-2(1H)-yl)-2-ethylbenzamide (4a), N-(6,7-Dimethoxy-3,4-dihydroisoquinolin-2(1H)-yl)-4-ethylbenzamide (4b), 4-Ethyl-N-(1-isopropyl-6, 7-dimethoxy-3,4-dihydroisoquinolin-2(1H)-yl)benzamide (4c), N-(7-Cyano-3,4-dihydroisoquinolin-2(1H)-yl)-4-ethylbenzamide (4d), N-(6-Chloro-3,4-dihydroisoquinolin-2(1H)-yl)-4-ethylbenzamide (4e), methyl-2-(4-ethylbenzamido)-6-((4-ethylbenzoyl)oxy)-1,2,3,4-tetrahydroisoquinoline-1-carboxylate (4f), and N-(7-Chloro-3,4-dihydroisoquinolin-2(1H)-yl)-4-ethylbenzamide (Redda-EVK-I-132).

In some embodiments of this aspect of the disclosure, the substituted tetrahydroisoquinoline ethylbenzamide is selected from the group consisting of:

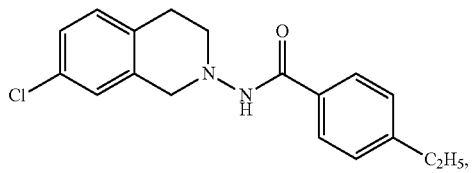

Redda-EVK-I-132

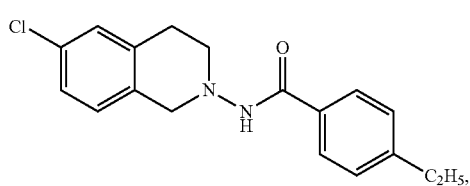

4e

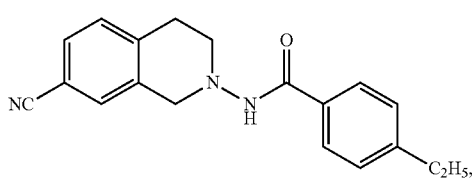

4d

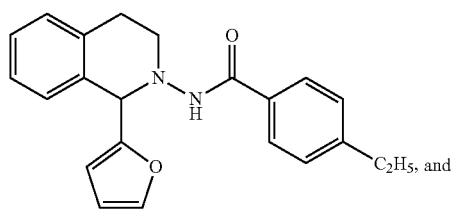

Redda-EVK-I-135

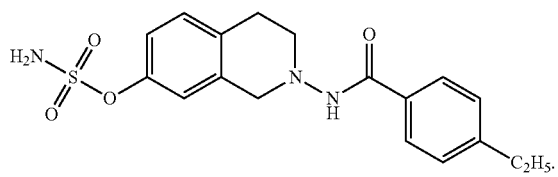

Redda-GM-4-171.

In some embodiments of this aspect of the disclosure, the substituted tetrahydroisoquinoline ethylbenzamide has the formula:

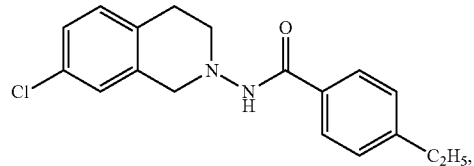

Redda-EVK-I-132

In some embodiments of this aspect of the disclosure, wherein the pharmaceutically acceptable composition is formulated to provide an amount of the substituted tetrahydroisoquinoline ethylbenzamide effective in inhibiting the proliferation of a cancer cell cultured in vitro.

In some embodiments of this aspect of the disclosure, the cell can be a breast cancer cell.

In some embodiments of this aspect of the disclosure, the pharmaceutically acceptable composition can be formulated to provide a therapeutically effective amount of the substituted tetrahydroisoquinoline ethylbenzamide for inhibiting the proliferation of a cell in vivo.

In some embodiments of this aspect of the disclosure, the cell can be a cancer cell.

In some embodiments of this aspect of the disclosure, the cell can be a breast cancer cell.

Yet another aspect of the disclosure encompasses embodiments of a method of inhibiting the proliferation of a cell comprising contacting a cell with an effective amount of a substituted tetrahydroisoquinoline ethylbenzamide having the formula I:

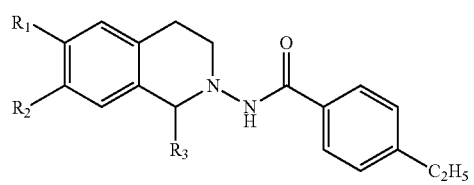

I wherein: when $R_2$ and $R_3$ are each hydrogen, $R_1$ can be a halogen; when $R_1$ and $R_3$ are each hydrogen, $R_2$ can be selected from the group consisting of a halogen, a cyano, or a sulfamate; and when $R_1$ and $R_2$ are each a hydrogen, $R_3$ can be a furyl group; and a pharmaceutically acceptable carrier, thereby reducing the proliferation rate of the cell compared to the proliferation rate of a cell not in contact with the compound.

In some embodiments of this aspect of the disclosure, the substituted tetrahydroisoquinoline ethylbenzamide, is selected from the group consisting of N-(7-hydroxy-3,4-dihydroisoquinolin-2(1H)-yl)-4-methoxybenzamide (2d), N-(7-hydroxy-3,4-dihydroisoquinolin-2(1H)-yl)-3-methoxybenzamide (2e), N-(7-hydroxy-3,4-dihydroisoquinolin-2(1H)-yl)-2-methoxybenzamide (2f), 4-Ethyl-N-(6-hydroxy-3,4-dihydroisoquinolin-2(1H)-yl) benzamide (2h), 4-Ethyl-N-(8-hydroxy-3,4-dihydroisoquinolin-2(1H)-yl) benzamide (2i), N,N'-(3,4-dihydroisoquinoline-2,8(1H)-diyl)bis(4-ethylbenzamide) (2j), N-(8-amino-3,4-dihydroisoquinolin-2(1H)-yl)-4-ethylbenzamide (2k), 4-Amino-N-(7-bromo-3,4-dihydroisoquinolin-2(1H)-yl) benzamide (2l), 4-(Ethylbenzamido)-1,2,3,4-tetrahydroisoquinolin-7-yl 4-ethylbenzoate (2m), 4-(tert-butyl)-N-(5-Methoxy-3,4-dihydroisoquinolin-2(1H)-yl) benzamide (3a), 4-(tert-butyl)-N-(5-Hydroxy-3,4-dihydroisoquinolin-2(1H)-yl) benzamide (3b), N,N'-(3,4-Dihydroisoquinoline-2,5(1H)-diyl)bis(4-ethylbenzamide) (3c), N-(5-Acetamido-3,4-dihydroisoquinolin-2(1H)-yl)-4-ethylbenzamide (3d), N-(5-(Benzyloxy)-3,4-dihydroisoquinolin-2(1H)-yl)-4-(tertbutyl) benzamide (3e), 4-Ethyl-N-(5-hydroxy-3,4-dihydroisoquinolin-2(1H)-yl) benzamide (3f), methyl-2-(4-ethylbenzamido)-1,2,3,4-tetrahydroisoquinoline-6-carboxylate (3h), 2-(4-Ethylbenzamido)-1,2,3,4-tetrahydroisoquinoline-6-carboxylic acid (3k), 2-(4-Methoxyphenylsulfonamido)-1,2,3,4-tetrahydroisoquinolin-5-yl-4-methoxybenzene-sulfonate (3l), N-(7-Cyano-3,4-dihydroisoquinolin-2(1H)-yl)-2-ethylbenzamide (4a), N-(6,7-Dimethoxy-3,4-dihydroisoquinolin-2(1H)-yl)-4-ethylbenzamide (4b), 4-Ethyl-N-(1-isopropyl-6,7-dimethoxy-3,4-dihydroisoquinolin-2(1H)-yl)benzamide (4c), N-(7-Cyano-3,4-dihydroisoquinolin-2(1H)-yl)-4-ethylbenzamide (4d), N-(6-Chloro-3,4-dihydroisoquinolin-2(1H)-yl)-4-ethylbenzamide (4e), methyl-2-(4-ethylbenzamido)-6-((4-ethylbenzoyl)oxy)-1,2,3,4-tetrahydroisoquinoline-1-carboxylate (4f), and N-(7-Chloro-3,4-dihydroisoquinolin-2(1H)-yl)-4-ethylbenzamide (Redda-EVK-I-132).

In some embodiments of this aspect of the disclosure, the substituted tetrahydroisoquinoline ethylbenzamide can have the formula:

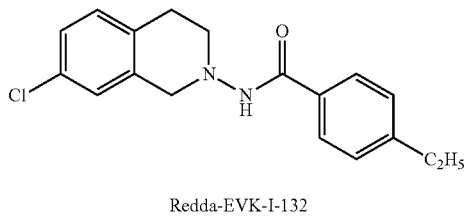 [SMILES: CCc1ccc(C(=O)NN2CCc3ccc(Cl)cc3C2)cc1]

Redda-EVK-I-132

In some embodiments of this aspect of the disclosure, the cell can be a cancer cell.

In some embodiments of this aspect of the disclosure, the cell can be a breast cancer cell.

In some embodiments of this aspect of the disclosure, the cell can be a cultured cell or a cell of an animal or human subject.

BRIEF DESCRIPTION OF THE DRAWINGS

Further aspects of the present disclosure will be more readily appreciated upon review of the detailed description of its various embodiments, described below, when taken in conjunction with the accompanying drawings.

Evaluation of the anti-proliferative activity of these compounds against human Ishikawa endometrial cell line showed that compounds 2d-2e, 2i-2m, 4d and 4e were more potent than TAM $IC_{50}$=7.87 µg/mL (Table 1). These results indicate some of the compounds of the disclosure may lower the risk of developing uterine cancer based upon the $IC_{50}$ value in comparison with TAM (Suresh et al., (2014) *Lett. Drug Des. Discov.* 11: 428-436).

Figure 13:
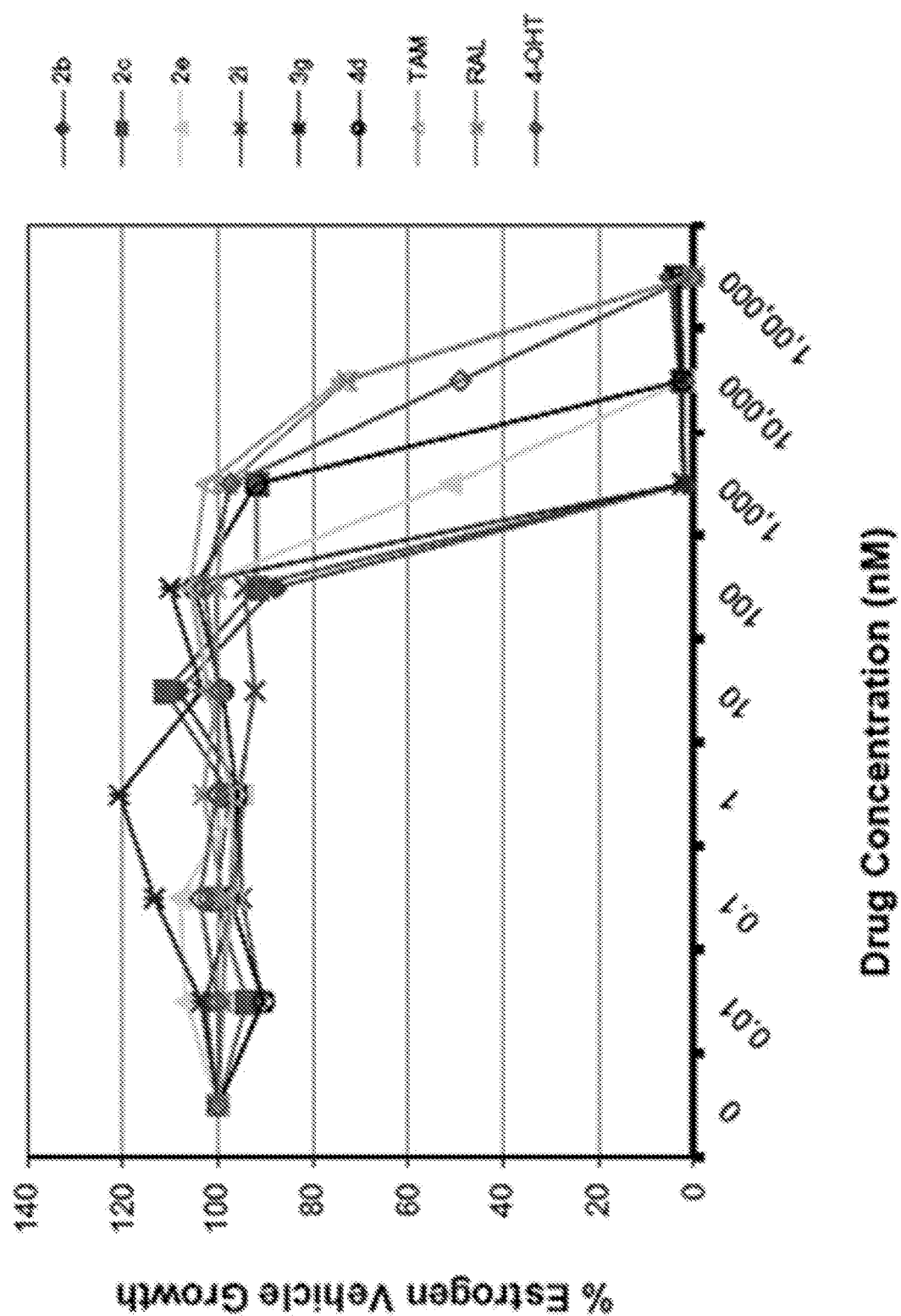

FIG. 13 is a graph illustrating in vitro antiproliferative activity of selective compounds against Ishikawa cell line.

Figure 14:
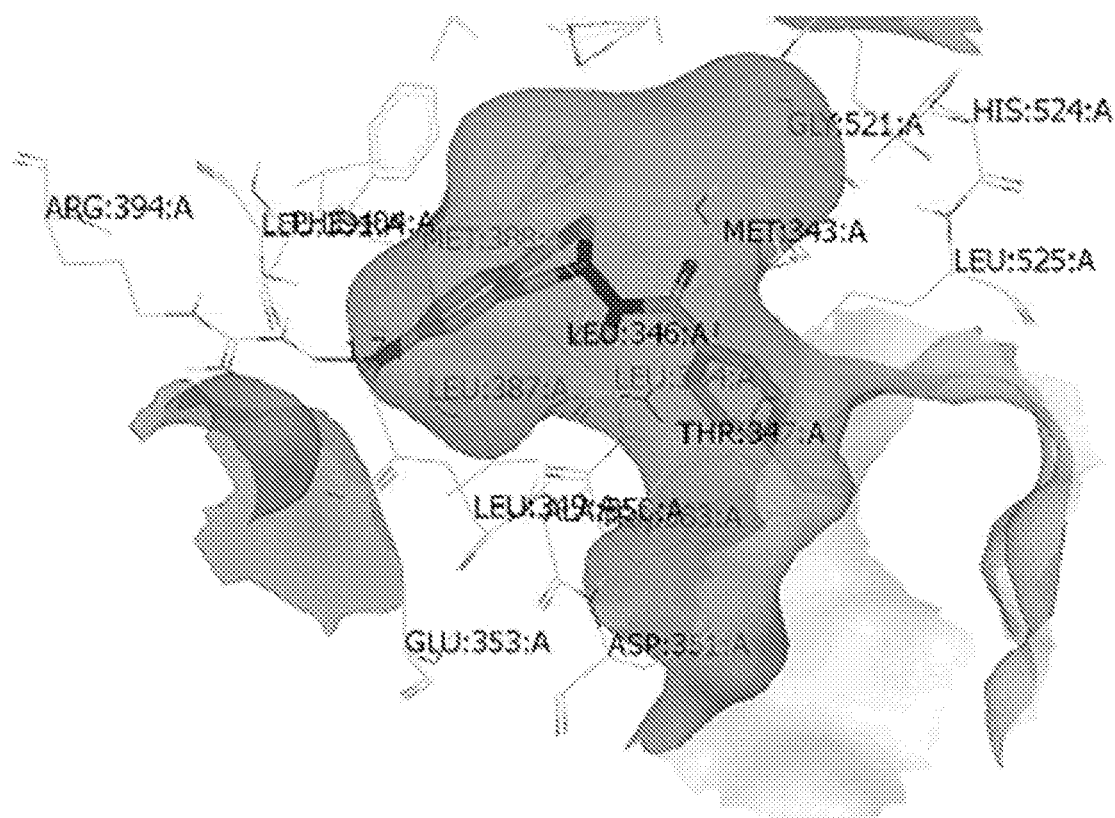

FIG. 14 illustrates the top scoring binding pose of the substituted THIQ (2b) at the active site of ERα-4-OHT complex (3eRT).

Figure 15:
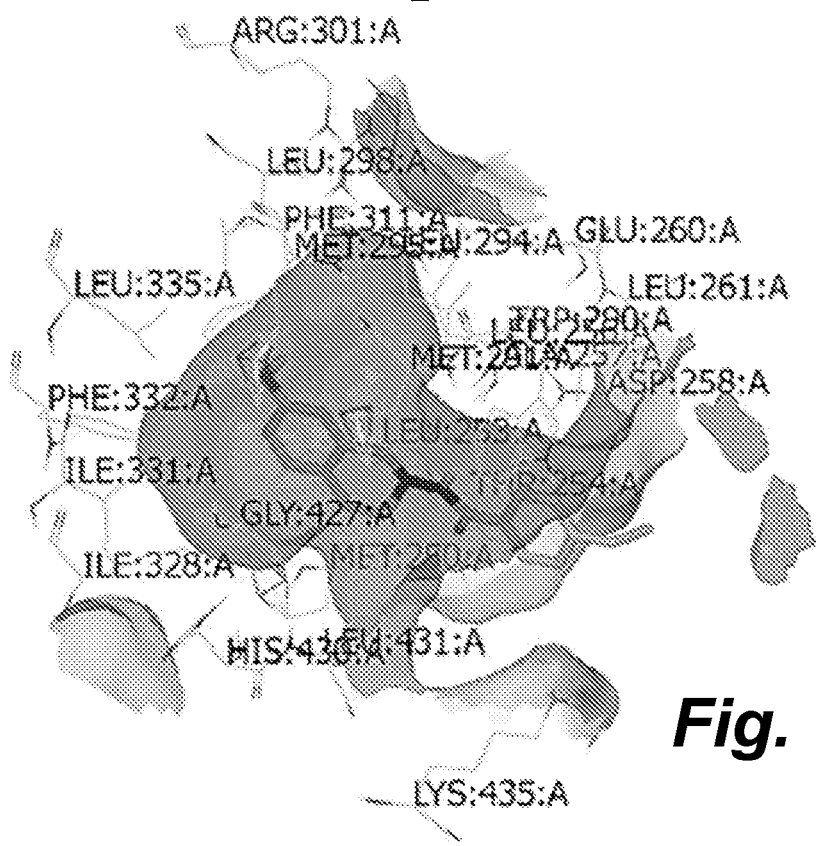

FIG. 15 illustrates the top scoring binding pose of the substituted THIQ (2b) at the active site of ERβ-RAL complex (1QKN).

Figure 16:
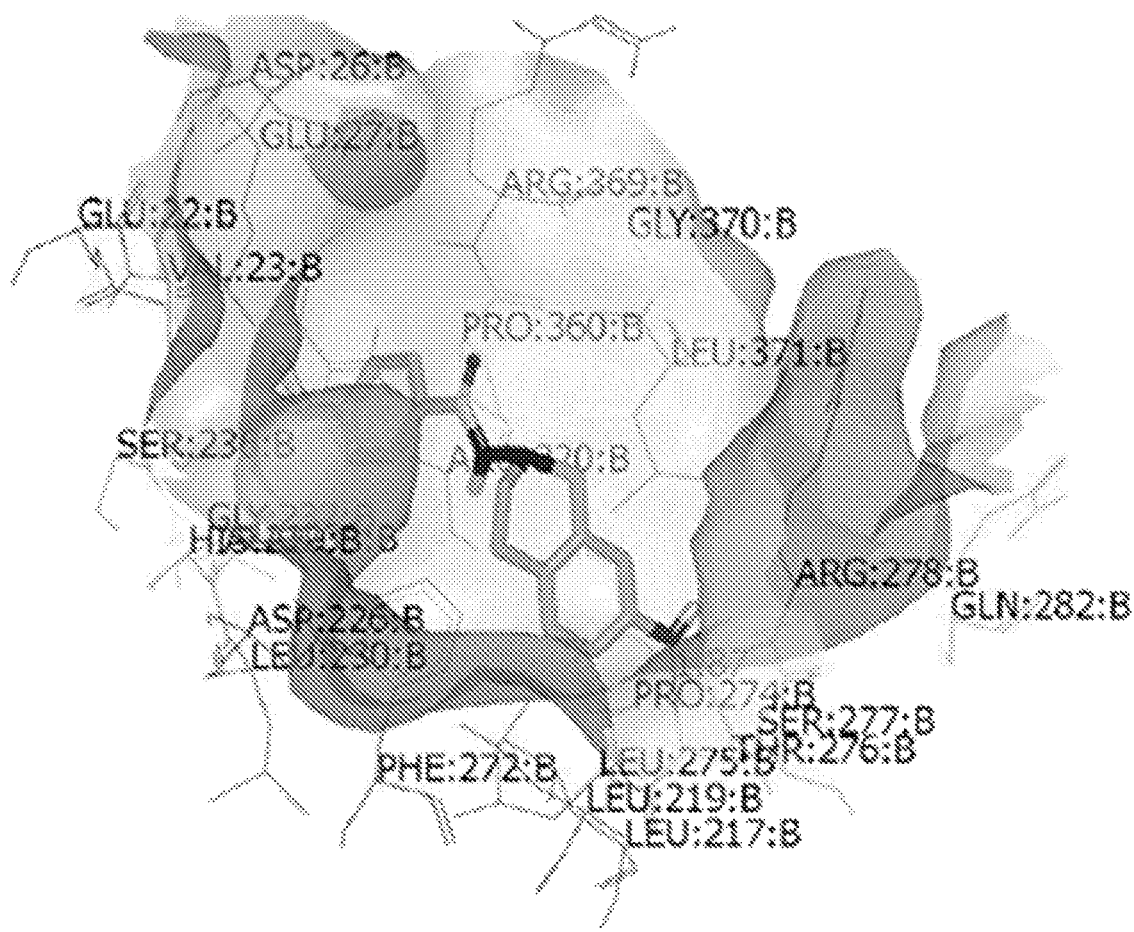

FIG. 16 illustrates the top scoring binding pose of the substituted THIQ (2b) at the active site of alpha-beta tubulin taxol.

Figure 17:
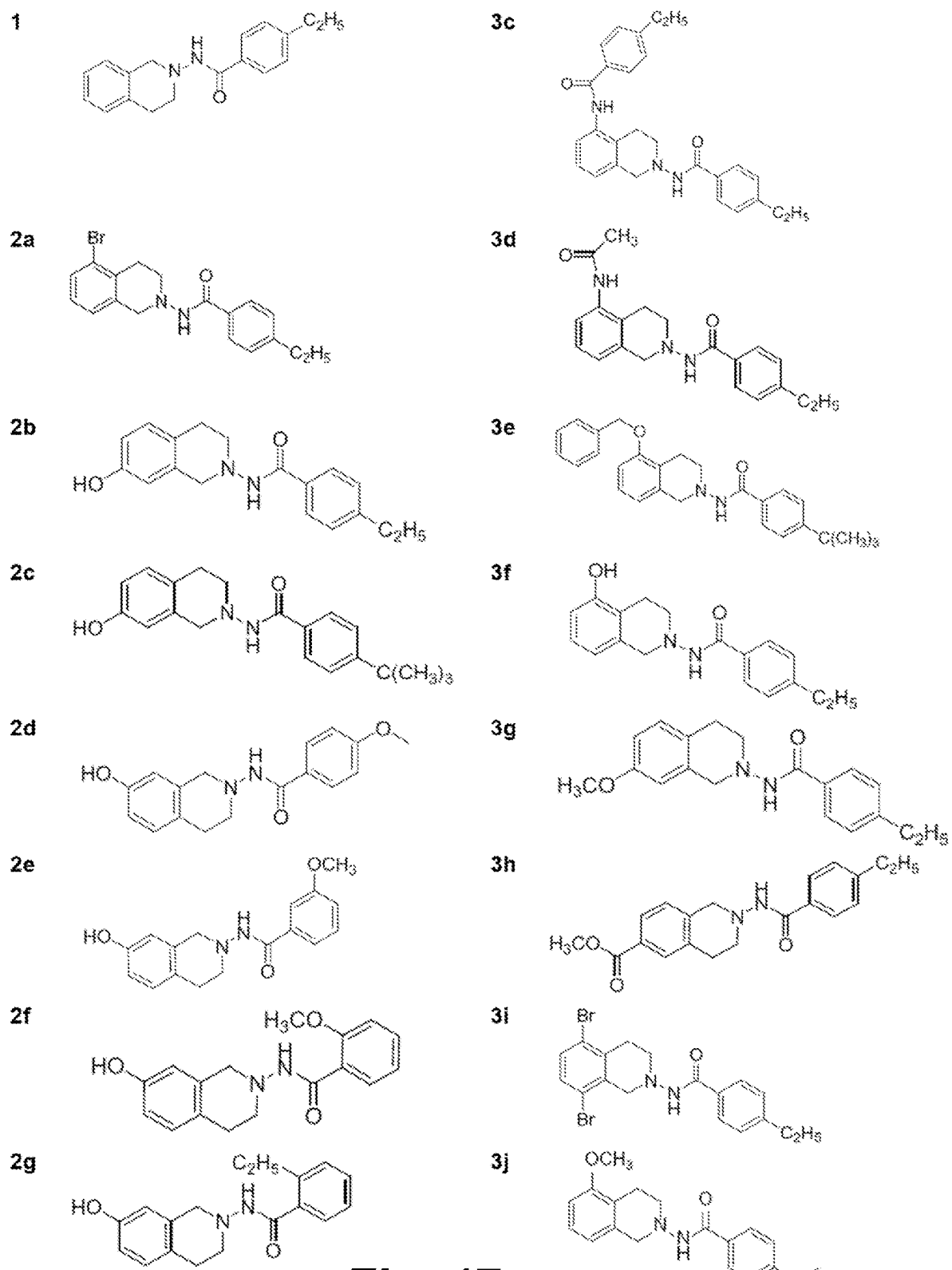

FIG. 17 illustrates the structures of the compounds of the disclosure.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

DEFINITIONS

The term "alkyl", either alone or within other terms such as "thioalkyl" and "arylalkyl", means a monovalent, saturated hydrocarbon radical which may be a straight chain (i.e. linear) or a branched chain. An alkyl radical for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-actyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the disclosure an alkyl radical is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl radical may be optionally substituted with substituents as defined herein at positions that do not significantly interfere with the preparation of compounds of the disclosure and do not significantly reduce the efficacy of the compounds. In certain aspects of the disclosure, an alkyl radical is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g., $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

In aspects of the disclosure, "substituted alkyl" includes an alkyl group substituted by, for example, one to five substituents, and preferably 1 to 3 substituents, such as alkyl, alkoxy, oxo, alkanoyl, aryl, aralkyl, aryloxy, alkanoyloxy, cycloalkyl, acyl, amino, hydroxyamino, alkylamino, arylamino, alkoxyamino, aralkylamino, cyano, halogen, hydroxyl, carboxyl, carbamyl, carboxylalkyl, keto, thioketo, thiol, alkylthiol, arylthio, aralkylthio, sulfonamide, thioalkoxy; and nitro.

The term "halogen" as used herein refers to a halogen such as fluorine, chlorine, bromine or iodine atoms.

The term "hydroxyl" or "hydroxy" as used herein refers to an —OH group.

The term "alkoxy" refers to a linear or branched oxy-containing radical having an alkyl portion of one to about ten carbon atoms, such as a methoxy radical, which may be substituted. In aspects of the disclosure an alkoxy radical may comprise about 1-10, 1-8, 1-6 or 1-3 carbon atoms. In embodiments of the disclosure, an alkoxy radical comprises about 1-6 carbon atoms and includes a $C_1$-$C_6$ alkyl-O-radical wherein $C_1$-$C_6$ alkyl has the meaning set out herein.

Examples of alkoxy radicals include without limitation methoxy, ethoxy, propoxy, butoxy, isopropoxy and tert-butoxy alkyls. An "alkoxy" radical may, optionally be substituted with one or more substituents disclosed herein including alkyl atoms to provide "alkylalkoxy" radicals; halo atoms, such as fluoro, chloro or bromo, to provide "haloalkoxy" radicals (e.g., fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" radicals (e.g., fluoromethoxymethyl, chloromethoxyethyl, trifluorornethoxymethyl, difluoromethoxyethyl, and trifluoroethoxymethyl).

The term "aryl", alone or in combination, as used herein refers to a carbocyclic aromatic system containing one, two or three rings wherein such rings may be attached together in a pendant manner or may be fused, in aspects of the disclosure an aryl radical comprises 4 to 24 carbon atoms, in particular 4 to 10, 4 to 8, or 4 to 6 carbon atoms. Illustrative "aryl" radicals includes without limitation aromatic radicals such as phenyl, benzyl, naphthyl, indenyl, benzocyclooctenyl, benzocycloheptenyl, pentalenyl, azulenyl, tetrahydronaphthyl, indanyl, biphenyl, acenaphthylenyl, fluorenyl, phenalenyl, phenanthrenyl, and anthracenyl, preferably phenyl.

An aryl radical may be optionally substituted with groups as disclosed herein, in particular hydroxyl, alkyl, carbonyl, carboxyl, thiol, amino, and/or halo, in particular a substituted aryl includes without limitation arylamine and arylalkylamine.

The term "substituted aryl" as used herein includes an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl, chlorphenyl and the like.

The term "carbonyl", whether used alone or with other terms, such as "aminocarbonyl", denotes —(C═O)—.

The term "cancer" as used herein shall be given its ordinary meaning and is a general term for diseases in which abnormal cells divide without control. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue, such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous) or malignant (cancerous). Different types of solid tumors are named for the type of cells that form them. Examples of solid tumors are sarcomas, carcinomas, and lymphomas. Leukemias (cancers of the blood) generally do not form solid tumors. Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, and cervical cancer.

The term "composition" as used herein encompasses a product comprising the specified ingredients in the specified amounts, as well as any product that results, directly or indirectly, from combinations of the specified ingredients in the specified amounts.

The term "excipient" as used herein refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "effective amount" and "therapeutically-effective amount" as used herein mean that amount of a compound, material, or composition comprising a compound or composition of the present disclosure, and which is effective for producing a desired therapeutic effect, biological or medicinal response in a tissue system, animal or human that is being sought by a researcher, veterinarian, medical doctor or other clinician, which includes alleviation of the symptoms of the disease or disorder being treated.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or an encapsulating material such as liposomes, polyethylene glycol (PEG), PEGylated liposomes, nanoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include, but are not limited to: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The terms "subject" and "animal or human subject" as used herein refers to any human or non-human animal to which a composition according to the disclosure may be delivered or administered.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

ABBREVIATIONS

ER, estrogen receptor; PR, progesterone receptor; SERM, Selective Estrogen Receptor Modulator; 1-MeTIQ, 1-Methyl-I, 2, 3, 4-tetrahydraisoquinoline; DMF, dimethylformamide; RT, room temperature; TAM, tamoxifen; RAL, raloxifene; 4-OHT, 4-Hydroxytamoxifen; THIQ, tetrahydroisoquinoline; TLC, thin layer chromatography; $CDCL_3$, deuterated chloroform; THF, tetrahydrofuran; $Et_3N$, trimethylamine.

DISCUSSION

The disclosure encompasses embodiments of ring substituted THIQs having anti-proliferative activities against human breast cancer cell lines and Ishikawa human endometrial adenocarcinoma cell lines. Tamoxifen (TAM), Raloxifene (RAL) and 4-Hydroxytamoxifen (4-OHT) were used as reference compounds. In-silico docking analysis and probable binding modes of these compounds were determined by mapping the active sites of the ER-α-4-OHT complex (PDB: 3eRT), ER-β-RAL complex (PDB: 1QKN), and α-β Tubulin-Taxol complex (PDB: 1JFF).

Accordingly, the present disclosure encompasses embodiments of a series of potent substituted tetrahydroisoquinoline (THIQ) moieties synthesized and characterized using NMR, IR and elemental analysis. Numerous substituted THIQs were systematically synthesized employing molecular design and structure activity relationship studies (Suresh et al., (2014) *Lett. Drug Design & Discov.* 11: 428-436; Gangapuram et al., (2014) *J. Cancer Sci. Ther.* 6: 161-169). The compounds' cytotoxic effects on MCF-7 (estrogen receptor positive breast cancer) cell lines, MDA-MB-231 (estrogen receptor negative breast cancer) cell lines and Ishikawa cell lines using CellTiter-Glo (CTG) luminescent cell viability essay were studied. The tests were done on different concentrations of the compounds ranging from 0.01 to 100,000 nM on 5000 MCF-7 cells/well, on 5000 MDA-MB-231 cells/well and on 5000 Ishikawa cells/well. Drug exposed cells were incubated at 37° C. for three days followed by CTG assay. Then $IC_{50}$ values were generated from Graph Pad Prism 4.

Figure 1:
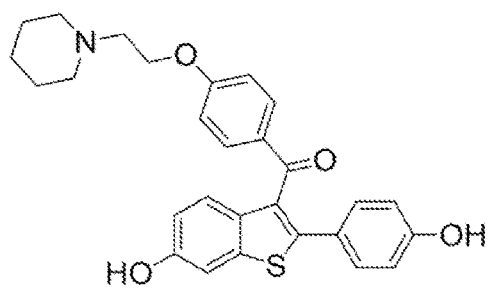
FIG. 1 illustrates prior art structures of anti-breast cancer agents in clinical use.
Figure 1:
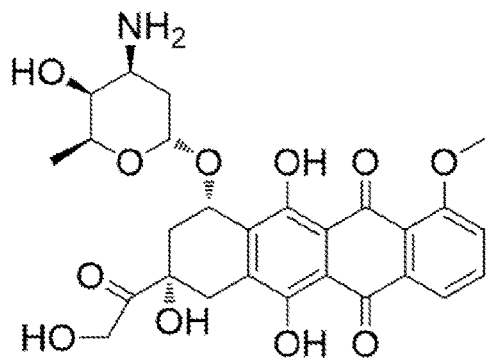
Figure 1:
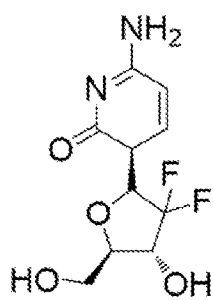
Figure 1:
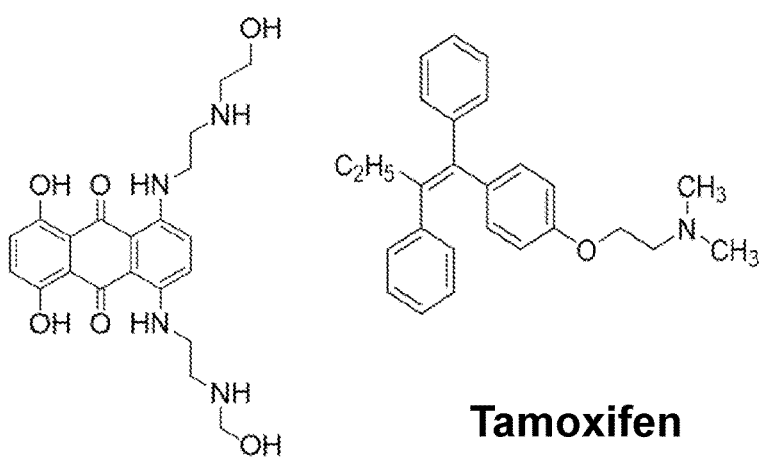
Figure 2:
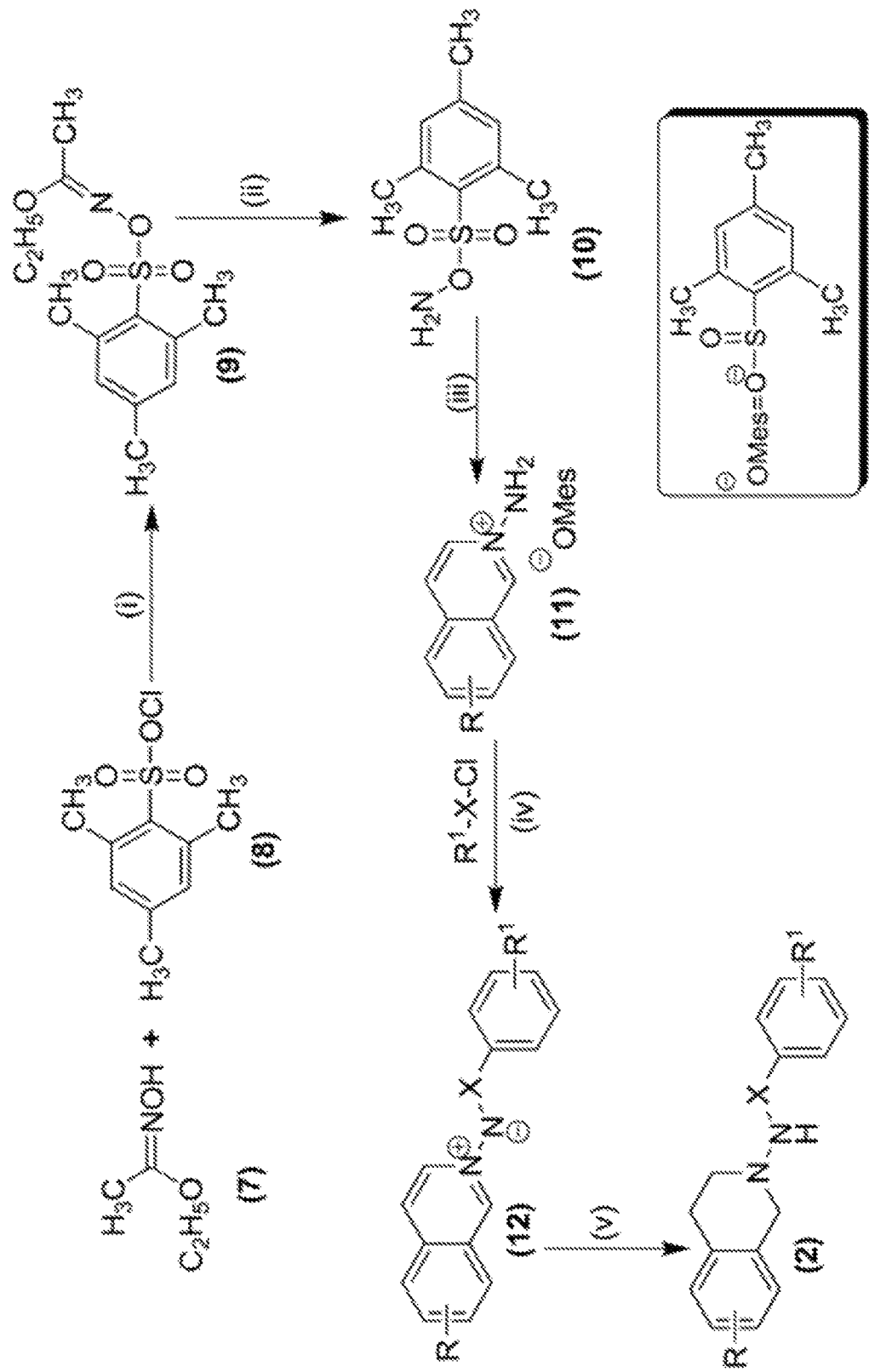
FIG. 2 illustrates the general procedure (Scheme 1) for the synthesis of substituted tetrahydroisoquinolinium-2,4,6-trimethyl benzene sulfonate (11a-11m). Reaction Conditions: (i) DMF, 0° C., 45 min, (ii) 70% $HClO_4$, p-dioxane, 0° C., 45 min, (iii) Substituted isoquinoline, dry $CH_2Cl_2$, 0° C., 5h, (iv) 4-substituted acyl/sulfonyl chlorides, dry THF, 70° C., 12h, (v) $NaBH_4$, abs. EtOH, 7 h; R=OH, Br, $NH_2$; X=CO, $SO_2$; $R^1$=4-$C_2H_5$, 3-$OCH_3$, 2-$OCH_3$, 2-$C_2H_5$
Figure 3:
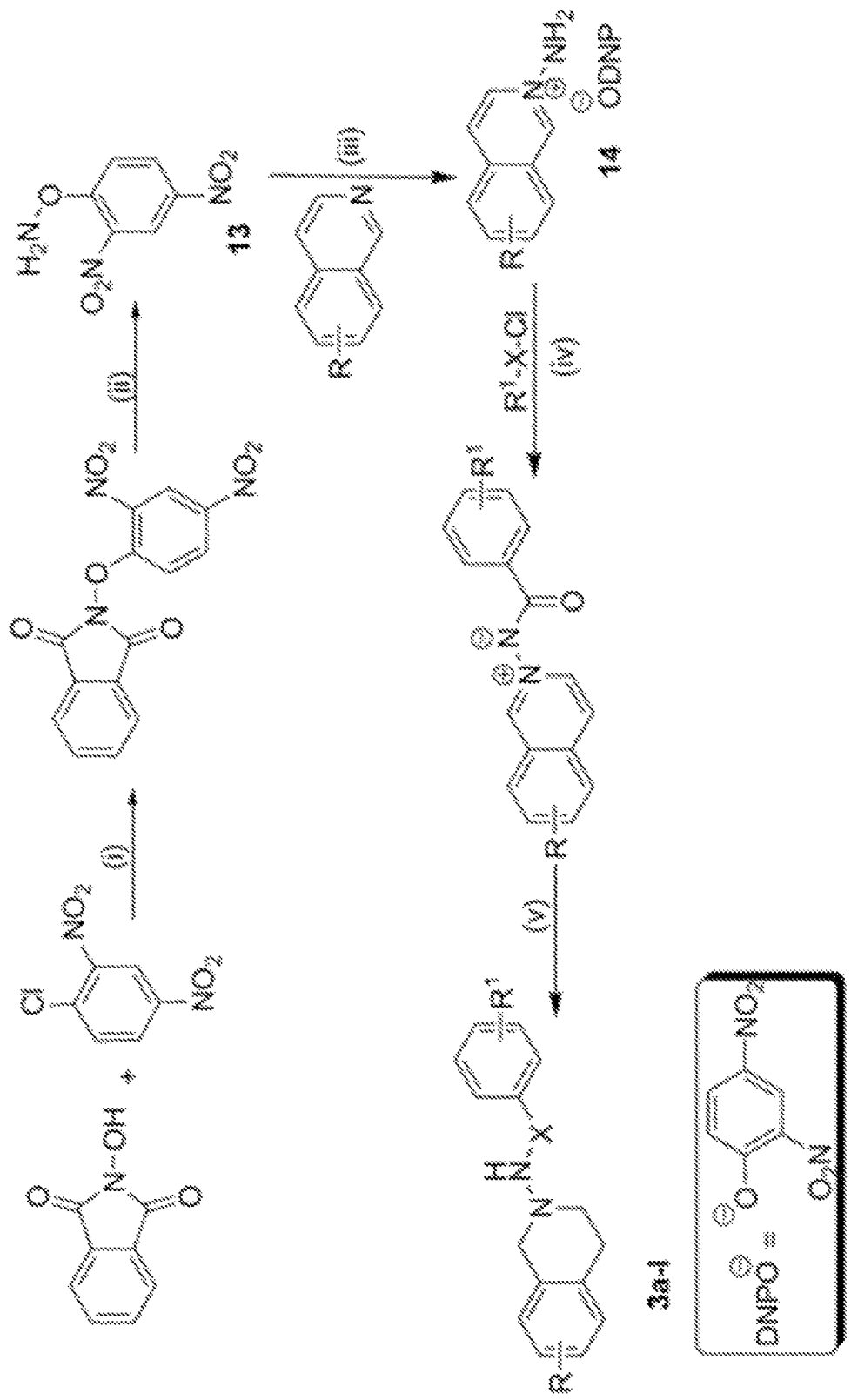
FIG. 3 illustrates a general procedure (Scheme 2) for the synthesis of substituted tetrahydroisoquinolines (THIQs) (3a-3l). Reaction Conditions: (i) $Et_3N$, RT, 2 hours, (ii) $NH_2.NH_2 \cdot H_2O$, $CH_2Cl_2$, MeOH, 0° C., (iii) $CH_3CN$, 50° C., (iv) $Et_3N$, THF, 25° C., (v) $NaBH_4$, EtOH, RT; X=CO, $SO_2$R=5-$OCH_3$, 5-OH, 5-$NHCOCH_3$, 5-NH—CO—$C_6H_4$-$C_2H_5$, 5-$OCH_2$—$C_6H_5$, 7-$OCH_3$, 7-$COOCH_3$, 5,8-di-Br, 6-COOH, 5-$OSO_2$—$C_6H_4$—$OCH_3$; $R_1$=4-$C(CH_3)_3$—$C_6H_4$, 4-$C_2H_5$-$C_6H_4$, 4-$OCH_3$—$C_6H_4$
Figure 4:
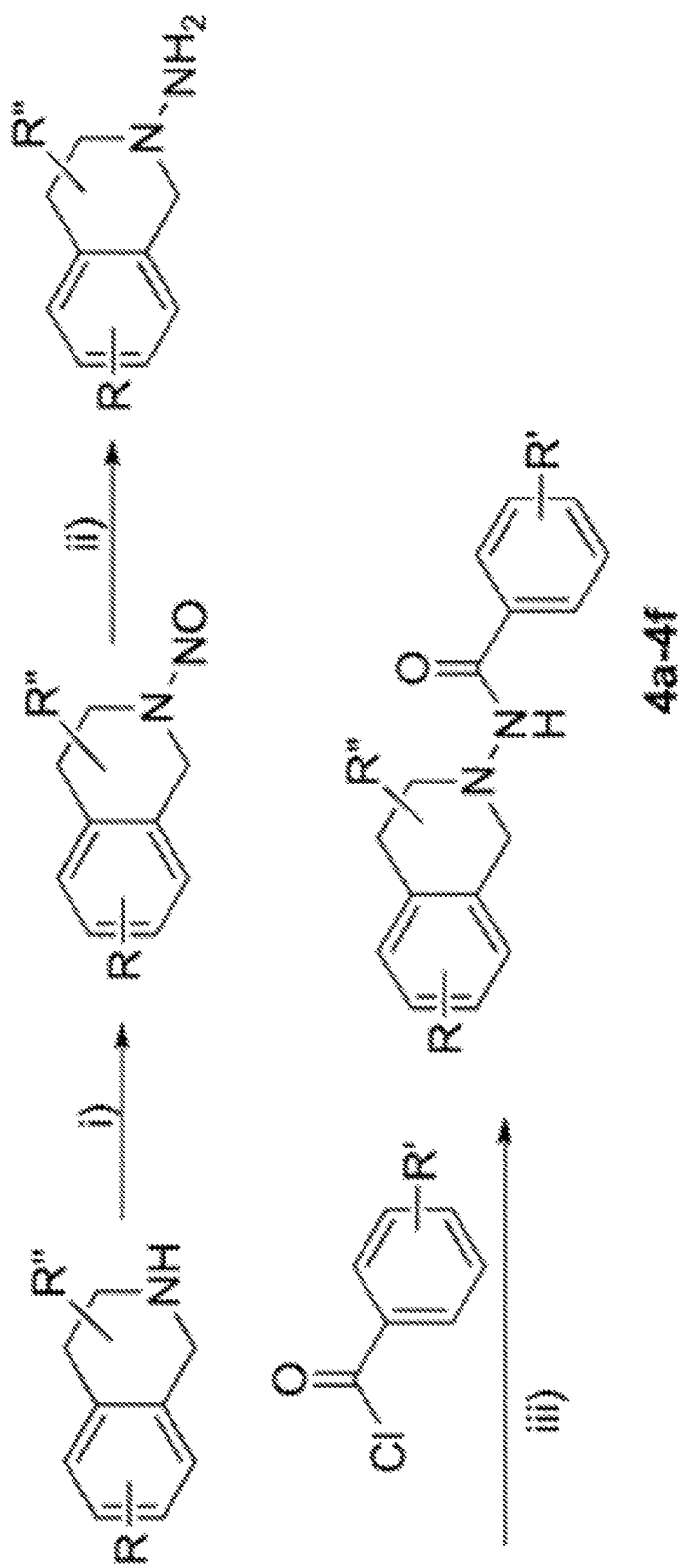
FIG. 4 illustrates the general procedure (Scheme 3) for the synthesis of substituted tetrahydroisoquinolines (THIQs) (4a-4f). Reaction Conditions: i) $NaNO_2$, $H_2O$, 0° C., ii) Zn, $CH_3COOH$, iii) Acyl Chlorides, $Et_3N$, THF; R=7-CN, 6,7-di-$OCH_3$, 6-Cl, 6-OCO—$C_6H_4$—$C_2H_5$; R'=4-$C_2H_5$—$C_6H_4$, R''=1-$CH(CH_3)_2$, 1-$COOCH_3$

Chemistry: Several substituted tetrahydroisoquinolines 2d-2m, 3h, 3k, 3l, and 4a-4f were prepared according to three different procedures as shown in Schemes 1, 2 and 3 (FIGS. 2-4). Compounds 2a-2m were synthesized following the Scheme 1 (FIG. 2). The aminating agent 10 was prepared using a reported procedure (Tamura et al., (1972) *J. Org. Chem.* 40: 4133-4135). The amino salts of ring substituted 2-aminoisoquinolinium mesitylenesulfonates of general structure 11 used in the present study were prepared by the reaction of substituted isoquinolines and the aminating agent 10 as previously reported (Gangapuram et al., (2014) *J. Cancer Sci. Ther.* 6: 161-169). Reaction of 11 with corresponding substituted acylating agents (acyl chlorides) afforded N-ylides 12a-12m as stable crystalline solids. Sodium borohydride reduction of N-ylides 12a-12m in absolute ethanol furnished the title compounds 2a-2m in fair to good yields. Compounds 3a-3l were synthesized following the Scheme 2 (FIG. 3). The aminating agent 13 was prepared using a reported procedure (Legault & Charette (2003) *J. Org. Chem.* 68: 7119-7122). The amino salts of ring substituted 2-aminoisoquinolinium compounds of general structure 14 were obtained with the reaction of the substituted isoquinolines and the aminating agent 13 in $CH_3CN$ heated at 50° C. for 24 hours. Without further purification, the salts were used to prepare the N-ylides by reaction with substituted acyl/sulfonyl chlorides. Final reduction of the ylides with sodium borohydride in absolute ethanol yielded the desired THIQs 3a-3l in moderate yields. Compounds 4a-4f were synthesized following the Scheme 3 (FIG. 4). N-Oxidation of commercially available ring substituted THIQs followed by the reduction of the NO group using standard zinc/acetic acid led to the synthesis of N-amino THIQs. Acylation reaction of the isolation of N-amino THIQs with substituted acyl chlorides in the presence of base (Et3N) yielded the desired substituted THIQs 4a-4f in low to moderate yields.

Antiproliferative activity: In vitro antiproliferative activity of compounds 2-4 and N-(7-Chloro-3,4-dihydroisoquinolin-2(1H)-yl)-4-ethylbenzamide (Redda-EVK-I-132) (as shown in FIG. 17) were evaluated against human MDA-MB-231 (ER negative breast carcinoma cell line), MCF-7 (ER positive breast cancer cell line) and Ishikawa (endometrial) cancer cell lines at concentration ranging from 0.01 nM to 100,000 nM in the presence of 10 nM estradiol (E2) using CellTiter-Glo assay (E2 was used for competitive growth inhibitory studies). As shown in Table 1, compounds 2b, 2i, and 3g. ($IC_{50}$=0.2 µg/mL, 0.08 µg/mL; 0.61 µg/mL, 0.09 µg/mL; 0.25 µg/mL, 0.11 µg/mL) against MCF-7 and Ishikawa cell lines, in comparison to TAM ($IC_{50}$=3.99 µg/mL, 7.87 µg/ml). (Note: $IC_{50}$ is the concentration of test drug where a 50% reduction is observed in cell growth compared to the untreated control after a 72 h period of exposure to test drug). This may be due to the differential affinity and binding levels of the ligand structural features to the ER receptors in the MCF-7 and Ishikawa cell lines.

Figure 11:
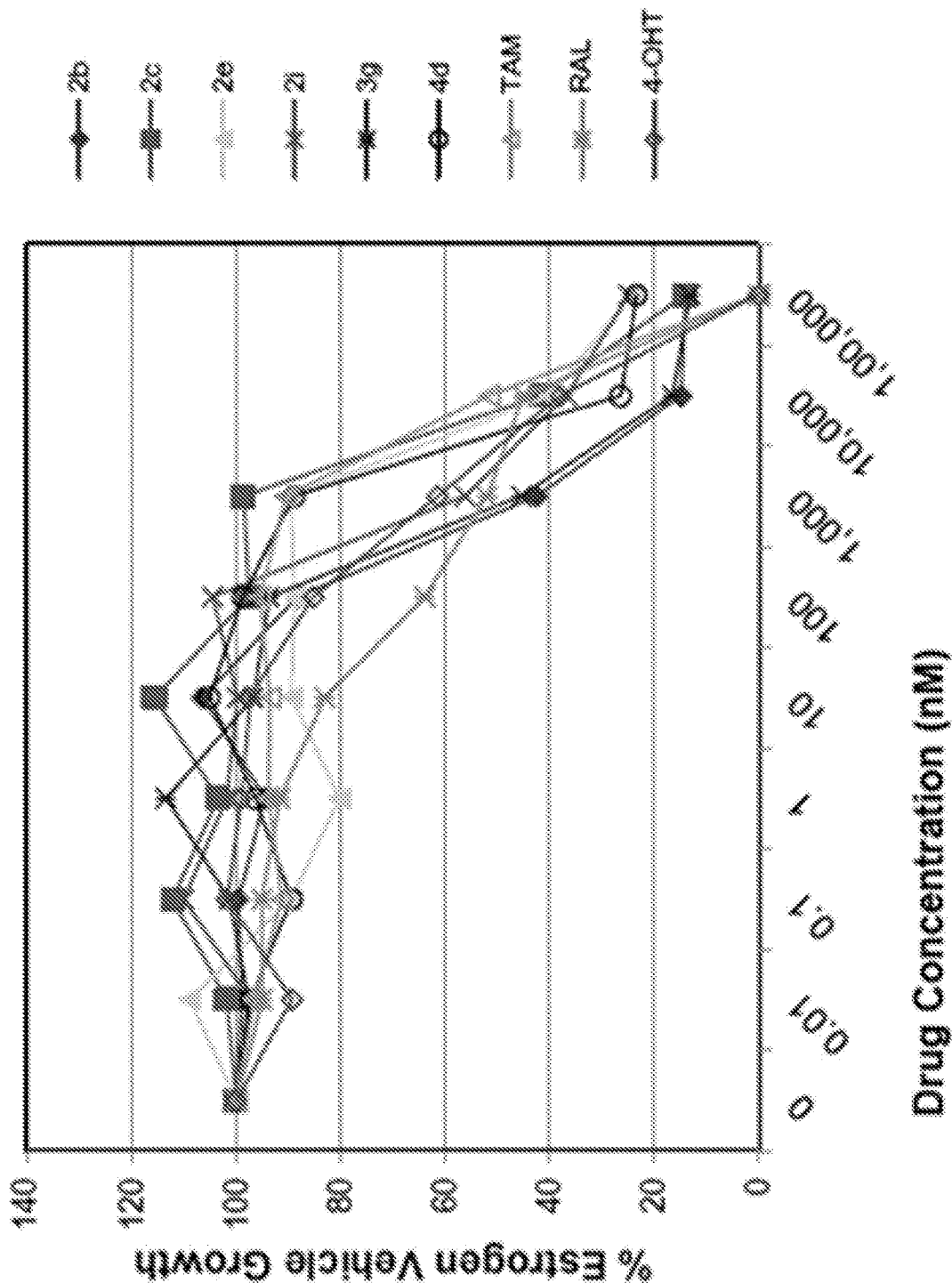
FIG. 11 is a graph illustrating in vitro antiproliferative activity of selective compounds against ER (+) MCF-7 cell line.
Figure 12:
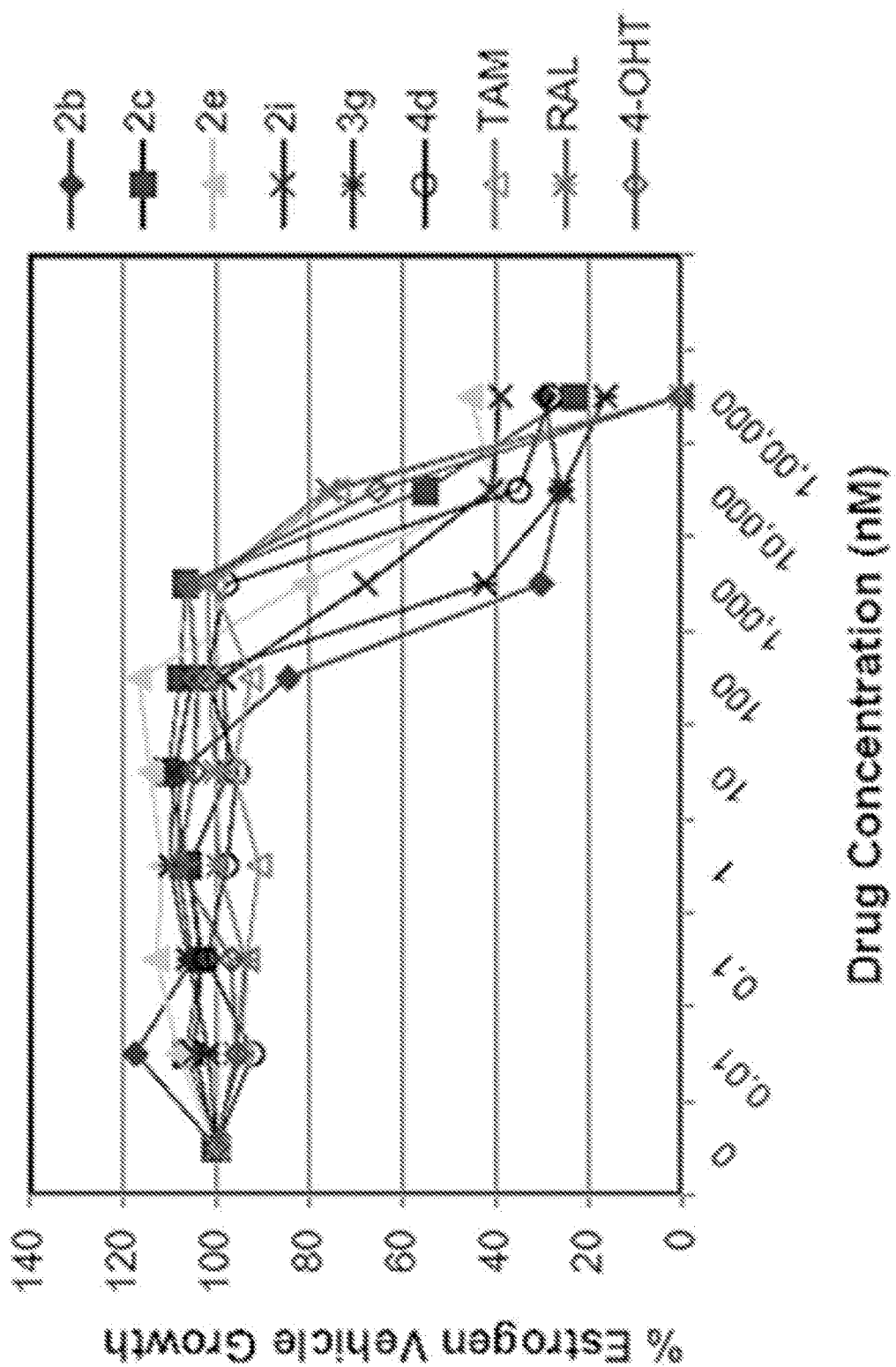
FIG. 12 is a graph illustrating in vitro antiproliferative activity of selective compounds against ER (−) MDA-MB-231 cell line.

Compounds bearing hydroxyl (—OH) substituents at 7th position (2b) and $8^{th}$ position (2i) proved to be very active of the series in this cell line and exhibit higher antiproliferative activity against MCF-7 cell line based on $IC_{50}$ value (FIG. 11). However, when the free hydroxyl group in compound (2b) was capped with a methyl group leading to compound (3g), the activity decreased marginally. However, the substituents at the $7^{th}$ position seem to be an ideal location for further manipulations of the lead compound (1). Compound (4d) with a cyano (CN) substitution at the $7^{th}$ position showed moderate activity ($IC_{50}$=1.28 µg/mL). Similarly, the ethyl substitution at the para position of the aryl-acyl ring leads to better activity than other substituents in that position and other positions on the ring.

TABLE 1

Antiproliferative activity of substituted Tetrahydroisoquinolines.

| | $IC_{50}$ µg/mL | | |
|---|---|---|---|
| Code | Ishikawa | MCF-7 | MDA-MB-231 |
| 1 | 0.01 | 0.43 | 0.37 |
| 2d | 0.99 | >29.83 | 25.17 |
| 2e | 0.31 | 1.86 | 1.71 |
| 2f | >29.83 | >29.83 | >29.83 |
| 2g | >29.64 | >29.64 | >29.64 |
| 2h | 22.38 | >29.64 | >29.64 |

TABLE 1-continued

Antiproliferative activity of substituted Tetrahydroisoquinolines.

| | IC$_{50}$ µg/mL | | |
|---|---|---|---|
| Code | Ishikawa | MCF-7 | MDA-MB-231 |
| 2i | 0.09 | 0.61 | 1.36 |
| 2j | 2.74 | 9.35 | 9.71 |
| 2k | 0.60 | 2.23 | 16.82 |
| 2l | 1.09 | 2.80 | 9.86 |
| 2m | 0.13 | 2.53 | 2.78 |
| 3a | >33.84 | >33.84 | >33.84 |
| 3b | 10.96 | 7.92 | 10.25 |
| 3c | 9.45 | 4.59 | 6.1 |
| 3d | >33.74 | >33.74 | >33.74 |
| 3e | >41.45 | >41.45 | >41.45 |
| 3f | 9.93 | 18.61 | 15.61 |
| 3h | 8.64 | 15.21 | 16.14 |
| 3k | >32.44 | >32.44 | >32.44 |
| 3l | >50.46 | >50.46 | >50.46 |
| 4a | >30.54 | 26.45 | >30.54 |
| 4b | >34.10 | >34.10 | >34.10 |
| 4c | 15.02 | >38.25 | >38.25 |
| 4d | 0.9 | 1.28 | 1.76 |
| 4e | 0.98 | 2.49 | 3.74 |
| 4f | 45.56 | >48.65 | >48.65 |
| Tamoxifen | 7.87 | 3.99 | 7.85 |
| Raloxifene-Hydrochloride | 10.53 | 0.98 | 11.21 |
| 4-Hydroxy Tamoxifen | 3.57 | 0.95 | 6.51 |

Compounds 2b and 3g with hydroxyl and methoxy substitutions on the 7$^{th}$ position of the THIQ phenyl ring proved to be more active than the lead structure (1). The other active compound in the series was compound (2i) where the hydroxyl substitution is on the 8th position of the THIQ phenyl ring. The poses adopted by compound (2i) in all three docking experiments reveal that this compound scored lower than the compounds (2b) and (3g). A hydrogen bonding interaction of its hydroxyl group with THR: 276(B) is observed in 1JFF but no hydrogen bonding with Arg: 394(A) was observed in 3eRT. Substitutions on the THIQ's aliphatic six membered rings (compounds 4c and 4f) proved to be completely inactive. Similarly, bis methoxy substitutions at 6$^{th}$ and 7$^{th}$ positions of the THIQ aromatic ring yielded inactive compounds. A comparison of the ethyl, t-butyl, methoxy substitutions on the acyl ring showed that the ethyl substituent at the 4-position (para) is the most optimal substitution for activity enhancement. Bis-acylated compounds 2j, 2m, 3c were less active whereas, 3d, 3l, and 4f were completely inactive. The lack of directed hydrogen bonding of compounds 2j, 2m, 3c, 3d, 3l, 4c, and 4f might be the reason for their biological inactivity.

Ring substituted THIQs based on the lead compound (1) were synthesized using three different synthetic methods in moderate yields and fully characterized. Their anti-proliferative activities against ER(+) MCF-7 and ER(-) MDA-

TABLE 2

Antiproliferative activity of substituted Tetrahydroisoquinolines.

| | | IC$_{50}$ µg/mL | | |
|---|---|---|---|---|
| Code | Structure | Ishikawa | MCF-7 | MDA-MB-231 |
| Redda-EVK-I-132 | 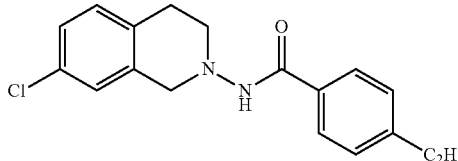 | 0.318 | 0.678 | 0.826 |
| Redda-EVK-I-135 | 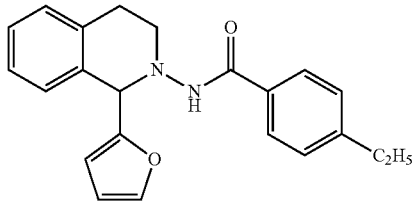 [SMILES: CCc1ccc(C(=O)NN2CCc3ccccc3C2c2ccco2)cc1] | 1.71 | 2.39 | 3.88 |
| Redda-GM-4-171 | 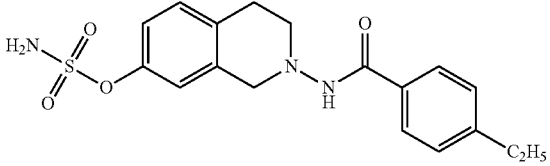 [SMILES: CCc1ccc(C(=O)NN2CCc3ccc(OS(N)(=O)=O)cc3C2)cc1] | 0.12 | 2.14 | 2.53 |

The antiproliferative activity of 31 new ring substituted THIQs (2, 3 and 4 series) were synthesized based on the lead structure (1) reported earlier, using three different synthetic approaches and were evaluated on MCF-7, MDA-MB-231, and Ishikawa cell lines. Their activities were compared with the reference drugs in the market, tamoxifen, 4-hydroxytamoxifen and raloxifene hydrochloride. In particular, the focus was on to examine the effects of the position and nature of substituents on the ring systems of lead THIQ (1). MB-231 breast cancer cell lines and Ishikawa cell lines were determined and compared to that of the standard drugs in the market tamoxifen, 4-hydroxytamoxifen and raloxifene. THIQs containing hydroxyl and methoxy substituents on the 7$^{th}$ position of the THIQ phenyl ring and ethyl substituent in the 4$^{th}$ position of the acyl ring proved to be promising and showed more activity compared to the lead compound (1).

However compound containing a hydroxyl substitution at the 8th position (2i) showed significant selectivity towards ER(+) MCF-7 breast cancer cell lines compared to ER(−) MDA-MB-231 cell lines indicating that this particular compound may be acting via ER dependent mechanism while compounds (2b) and (3g) may be acting via ER independent mechanisms. Recent studies have indeed showed that compound (2b) is a potent microtubule-destabilizing agent. Pose predictions and docking scores were compared for the active and inactive THIQs in the present study. The docking scores (Hybrid_Chemgauss scores) for the active THIQs were consistently higher than the inactive compounds. Within the active compounds, the scores agree with the experimental findings. Hydrogen bonding interactions between the amino acid residues of the receptors in the active site and the compounds containing OH substituents on the THQ phenyl ring were observed.

Accordingly, it is contemplated that the compounds of the present disclosure can be administered to a patient alone or as part of a pharmaceutically acceptable composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like. Solid dosage forms such as tablets, dragees, capsules, pills, and granules can be prepared with coatings and shells, such as enteric coatings and others well-known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like. Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present disclosure with suitable non-irritating excipients or carriers such as cocoa butter, polyethylene glycol, or a suppository wax, which are solid at ordinary temperatures but liquid at body temperature and therefore, melt in the rectum or vaginal cavity and release the active component.

Dosage forms for topical administration of a compound of this disclosure include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this disclosure.

The compounds of the present disclosure can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a number of factors including the requirements of the patient, the severity of the condition being treated, and the pharmacological activity of the compound being used. The determination of optimum dosages for a particular patient is well known to those skilled in the art.

The compounds of the present disclosure can exist in different stereoisomeric forms by virtue of the presence of asymmetric centers in the compounds. It is contemplated that all stereoisomeric forms of the compounds as well as mixtures thereof, including racemic mixtures, form part of this disclosure. In addition, the compounds of the present disclosure can exist in unsolvated as well as solvated forms with pharmaceutically acceptable solvents such as water, ethanol, and the like. In general, the solvated forms are considered equivalent to the unsolvated forms for the purposes of the present disclosure.

One aspect of the disclosure, therefore, encompasses embodiments of a substituted tetrahydroisoquinoline ethylbenzamide having the formula I:

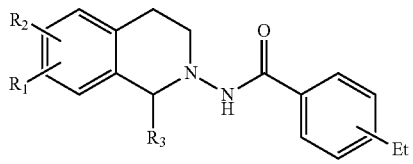

wherein: $R_1$ and $R_2$ can be each independently a hydrogen, a halogen, a methoxy, hydroxyl, cyano, an acyl, a sulfamate, an ethylbenzamide group, an ethylbenzoate group, or an acetamido group; $R_3$ can be hydrogen or a furyl group, wherein when $R_3$ is a furyl group, $R_1$ and $R_2$ are each a hydrogen.

In some embodiments of this aspect of the disclosure, when $R_1$ and $R_3$ are each hydrogen, $R_2$ can be a halogen, a cyano, or a sulfamate.

In some embodiments of this aspect of the disclosure, $R_2$ can be chlorine.

In some embodiments of this aspect of the disclosure, the substituted tetrahydroisoquinoline ethylbenzamide can be selected from the group consisting of N-(7-hydroxy-3,4-dihydroisoquinolin-2(1H)-yl)-4-methoxybenzamide (2d), N-(7-hydroxy-3,4-dihydroisoquinolin-2(1H)-yl)-3-methoxybenzamide (2e), N-(7-hydroxy-3,4-dihydroisoquinolin-2(1H)-yl)-2-methoxybenzamide (2f), 4-Ethyl-N-(6-hydroxy-3,4-dihydroisoquinolin-2(1H)-yl) benzamide (2h), 4-Ethyl-N-(8-hydroxy-3,4-dihydroisoquinolin-2(1H)-yl) benzamide (2i), N,N'-(3,4-dihydroisoquinoline-2,8(1H)-diyl)bis(4-ethylbenzamide) (2j), N-(8-amino-3,4-dihydroisoquinolin-2(1H)-yl)-4-ethylbenzamide (2k), 4-Amino-N-(7-bromo-3,4-dihydroisoquinolin-2(1H)-yl) benzamide (2l), 4-(Ethylbenzamido)-1,2,3,4-tetrahydroisoquinolin-7-yl 4-ethylbenzoate (2m), 4-(tert-butyl)-N-(5-Methoxy-3,4-dihydroisoquinolin-2(1H)-yl) benzamide (3a), 4-(tert-butyl)-N-(5-Hydroxy-3,4-dihydroisoquinolin-2(1H)-yl) benzamide (3b), N,N'-(3,4-Dihydroisoquinoline-2,5(1H)-diyl)bis(4-ethylbenzamide) (3c), N-(5-Acetamido-3,4-dihydroisoquinolin-2(1H)-yl)-4-ethylbenzamide (3d), N-(5-(Benzyloxy)-3,4-dihydroisoquinolin-2(1H)-yl)-4-(tertbutyl) benzamide (3e), 4-Ethyl-N-(5-hydroxy-3,4-dihydroisoquinolin-2(1H)-yl) benzamide (3f), 2-(4-Ethylbenzamido)-1,2,3,4-tetrahydroisoquinoline-6-carboxylic acid (3k), 2-(4-Methoxyphenylsulfonamido)-1,2,3,4-tetrahydroisoquinolin-5-yl-4-methoxybenzene-sulfonate (3l), N-(7-Cyano-3,4-dihydroisoquinolin-2(1H)-yl)-2-ethylbenzamide (4a), N-(6,7-Dimethoxy-3,4-dihydroisoquinolin-2(1H)-yl)-4-ethylbenzamide (4b), 4-Ethyl-N-(1-isopropyl-6,7-dimethoxy-3,4-dihydroisoquinolin-2(1H)-yl)benzamide (4c), N-(7-Cyano-3,4-dihydroisoquinolin-2(1H)-yl)-4-ethylbenzamide (4d), N-(6-Chloro-3,4-dihydroisoquinolin-2(1H)-yl)-4-ethylbenzamide (4e), methyl-2-(4-ethylbenzamido)-6-((4-ethylbenzoyl)oxy)-1,2,3,4-tetrahydroisoquinoline-1-carboxylate (4f), and N-(7-Chloro-3,4-dihydroisoquinolin-2(1H)-yl)-4-ethylbenzamide (Redda-EVK-I-132).

In some embodiments of this aspect of the disclosure, the substituted tetrahydroisoquinoline ethylbenzamide can be selected from the group consisting of:

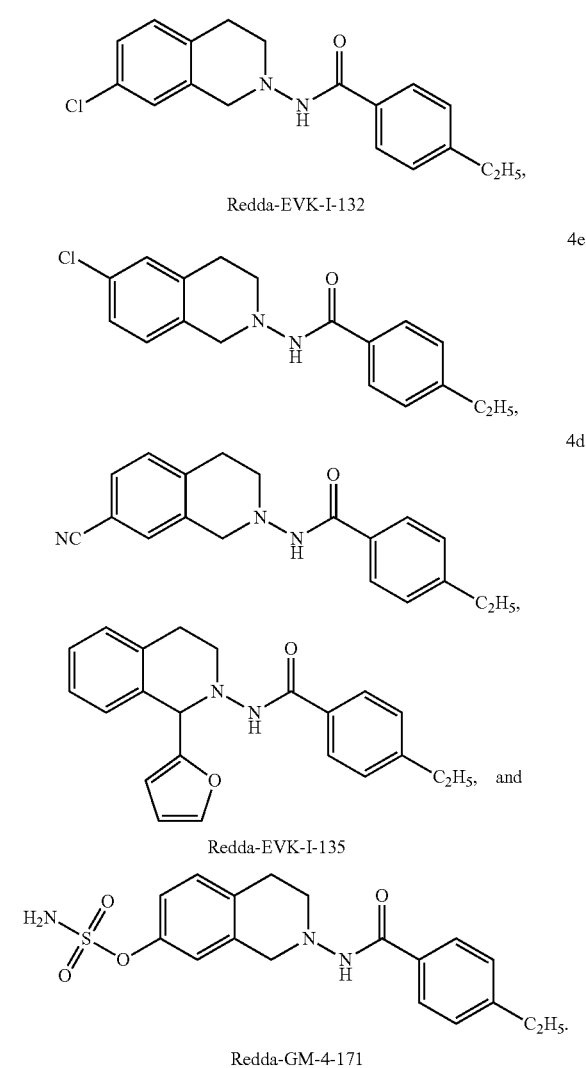

In some embodiments of this aspect of the disclosure, the substituted tetrahydroisoquinoline ethylbenzamide has the formula:

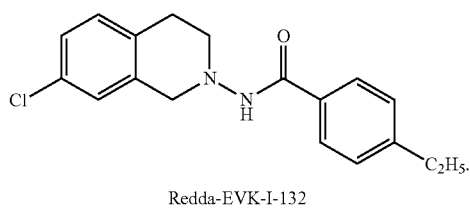 [SMILES: CCc1ccc(C(=O)NN2CCc3ccc(Cl)cc3C2)cc1]

Another aspect of the disclosure encompasses embodiments of a pharmaceutically acceptable composition comprising a substituted tetrahydroisoquinoline ethylbenzamide having the formula I:

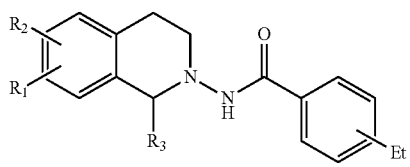

wherein: $R_1$ and $R_2$ can be each independently a hydrogen, a halogen, a methoxy, hydroxyl, cyano, an acyl, a sulfamate, an ethylbenzamide group, an ethylbenzoate group, or an acetamido group; $R_3$ can be hydrogen or a furyl group, wherein when $R_3$ is a furyl group, $R_1$ and $R_2$ are each a hydrogen; and a pharmaceutically acceptable carrier.

In some embodiments of this aspect of the disclosure, $R_1$ and $R_3$ are each hydrogen, $R_2$ can be a halogen, a cyano, or a sulfamate In some embodiments of this aspect of the disclosure, $R_2$ is chlorine.

In some embodiments of this aspect of the disclosure, the substituted tetrahydroisoquinoline ethylbenzamide can be selected from the group consisting of N-(7-hydroxy-3,4-dihydroisoquinolin-2(1H)-yl)-4-methoxybenzamide (2d), N-(7-hydroxy-3,4-dihydroisoquinolin-2(1H)-yl)-3-methoxybenzamide (2e), N-(7-hydroxy-3,4-dihydroisoquinolin-2 (1H)-yl)-2-methoxybenzamide (2f), 4-Ethyl-N-(6-hydroxy-3,4-dihydroisoquinolin-2(1H)-yl) benzamide (2h), 4-Ethyl-N-(8-hydroxy-3,4-dihydroisoquinolin-2(1H)-yl) benzamide (2i), N,N'-(3,4-dihydroisoquinoline-2,8(1H)-diyl)bis(4-ethylbenzamide) (2j), N-(8-amino-3,4-dihydroisoquinolin-2 (1H)-yl)-4-ethylbenzamide (2k), 4-Amino-N-(7-bromo-3,4-dihydroisoquinolin-2(1H)-yl) benzamide (2l), 4-(Ethylbenzamido)-1,2,3,4-tetrahydroisoquinolin-7-yl 4-ethylbenzoate (2m), 4-(tert-butyl)-N-(5-Methoxy-3,4-dihydroisoquinolin-2(1H)-yl) benzamide (3a), 4-(tert-butyl)-N-(5-Hydroxy-3,4-dihydroisoquinolin-2(1H)-yl) benzamide (3b), N,N'-(3,4-Dihydroisoquinoline-2,5(1H)-diyl)bis(4-ethylbenzamide) (3c), N-(5-Acetamido-3,4-dihydroisoquinolin-2 (1H)-yl)-4-ethylbenzamide (3d), N-(5-(Benzyloxy)-3,4-dihydroisoquinolin-2(1H)-yl)-4-(tertbutyl) benzamide (3e), 4-Ethyl-N-(5-hydroxy-3,4-dihydroisoquinolin-2(1H)-yl) benzamide (3f), 2-(4-Ethylbenzamido)-1,2,3,4-tetrahydroisoquinoline-6-carboxylic acid (3k), 2-(4-Methoxyphenylsulfonamido)-1,2,3,4-tetrahydroisoquinolin-5-yl-4-methoxybenzene-sulfonate (3l), N-(7-Cyano-3,4-dihydroisoquinolin-2(1H)-yl)-2-ethylbenzamide (4a), N-(6,7-Dimethoxy-3,4-dihydroisoquinolin-2(1H)-yl)-4-ethylbenzamide (4b), 4-Ethyl-N-(1-isopropyl-6,7-dimethoxy-3,4-dihydroisoquinolin-2(1H)-yl)benzamide (4c), N-(7-Cyano-3,4-dihydroisoquinolin-2(1H)-yl)-4-ethylbenzamide (4d), N-(6-Chloro-3,4-dihydroisoquinolin-2(1H)-yl)-4-ethylbenzamide (4e), methyl-2-(4-ethylbenzamido)-6-((4-ethylbenzoyl)oxy)-1,2,3,4-tetrahydroisoquinoline-1-carboxylate (4f), and N-(7-Chloro-3,4-dihydroisoquinolin-2(1H)-yl)-4-ethylbenzamide (Redda-EVK-I-132).

In some embodiments of this aspect of the disclosure, the substituted tetrahydroisoquinoline ethylbenzamide is selected from the group consisting of:

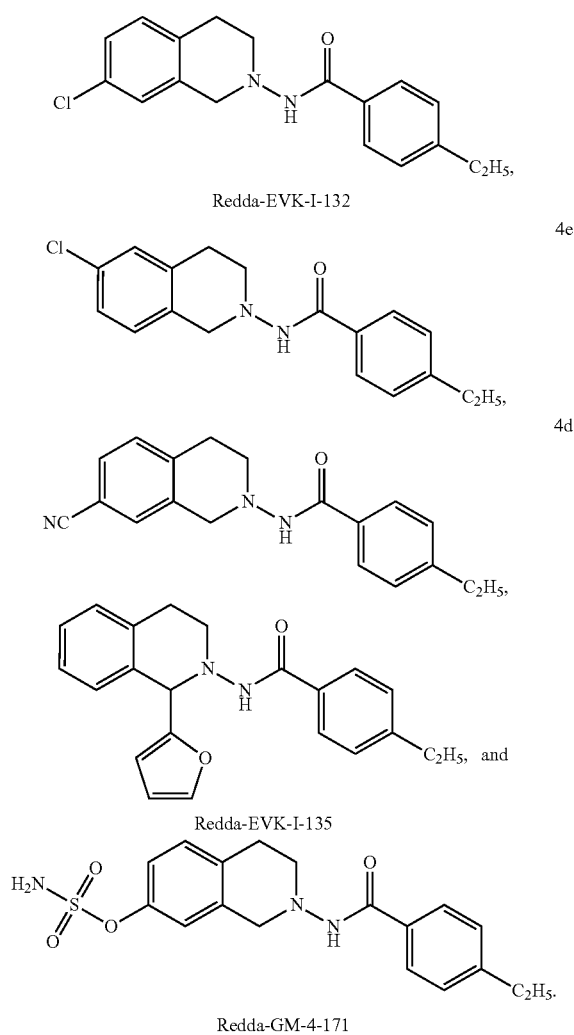

In some embodiments of this aspect of the disclosure, the substituted tetrahydroisoquinoline ethylbenzamide has the formula:

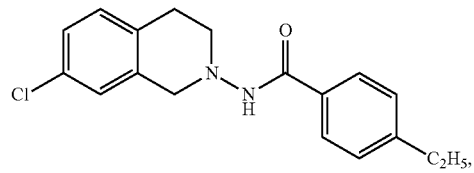

Redda-EVK-I-132

In some embodiments of this aspect of the disclosure, wherein the pharmaceutically acceptable composition is formulated to provide an amount of the substituted tetrahydroisoquinoline ethylbenzamide effective in inhibiting the proliferation of a cancer cell cultured in vitro.

In some embodiments of this aspect of the disclosure, the cell can be a breast cancer cell.

In some embodiments of this aspect of the disclosure, the pharmaceutically acceptable composition can be formulated to provide a therapeutically effective amount of the substituted tetrahydroisoquinoline ethylbenzamide for inhibiting the proliferation of a cell in vivo.

In some embodiments of this aspect of the disclosure, the cell can be a cancer cell.

In some embodiments of this aspect of the disclosure, the cell can be a breast cancer cell.

Yet another aspect of the disclosure encompasses embodiments of a method of inhibiting the proliferation of a cell comprising contacting a cell with an effective amount of a substituted tetrahydroisoquinoline ethylbenzamide having the formula I:

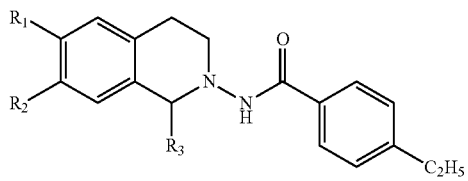

I wherein: when $R_2$ and $R_3$ are each hydrogen, $R_1$ can be a halogen; when $R_1$ and $R_3$ are each hydrogen, $R_2$ can be selected from the group consisting of a halogen, a cyano, or a sulfamate; and when $R_1$ and $R_2$ are each a hydrogen, $R_3$ can be a furyl group; and a pharmaceutically acceptable carrier, thereby reducing the proliferation rate of the cell compared to the proliferation rate of a cell not in contact with the compound.

In some embodiments of this aspect of the disclosure, the substituted tetrahydroisoquinoline ethylbenzamide, is selected from the group consisting of N-(7-hydroxy-3,4-dihydroisoquinolin-2(1H)-yl)-4-methoxybenzamide (2d), N-(7-hydroxy-3,4-dihydroisoquinolin-2(1H)-yl)-3-methoxybenzamide (2e), N-(7-hydroxy-3,4-dihydroisoquinolin-2(1H)-yl)-2-methoxybenzamide (2f), 4-Ethyl-N-(6-hydroxy-3,4-dihydroisoquinolin-2(1H)-yl) benzamide (2h), 4-Ethyl-N-(8-hydroxy-3,4-dihydroisoquinolin-2(1H)-yl) benzamide (2i), N,N'-(3,4-dihydroisoquinoline-2,8(1H)-diyl)bis(4-ethylbenzamide) (2j), N-(8-amino-3,4-dihydroisoquinolin-2(1H)-yl)-4-ethylbenzamide (2k), 4-Amino-N-(7-bromo-3,4-dihydroisoquinolin-2(1H)-yl) benzamide (2l), 4-(Ethylbenzamido)-1,2,3,4-tetrahydroisoquinolin-7-yl 4-ethylbenzoate (2m), 4-(tert-butyl)-N-(5-Methoxy-3,4-dihydroisoquinolin-2(1H)-yl) benzamide (3a), 4-(tert-butyl)-N-(5-Hydroxy-3,4-dihydroisoquinolin-2(1H)-yl) benzamide (3b), N,N'-(3,4-Dihydroisoquinoline-2,5(1H)-diyl)bis(4-ethylbenzamide) (3c), N-(5-Acetamido-3,4-dihydroisoquinolin-2(1H)-yl)-4-ethylbenzamide (3d), N-(5-(Benzyloxy)-3,4-dihydroisoquinolin-2(1H)-yl)-4-(tertbutyl) benzamide (3e), 4-Ethyl-N-(5-hydroxy-3,4-dihydroisoquinolin-2(1H)-yl) benzamide (3f), 2-(4-Ethylbenzamido)-1,2,3,4-tetrahydroisoquinoline-6-carboxylic acid (3k), 2-(4-Methoxyphenylsulfonamido)-1,2,3,4-tetrahydroisoquinolin-5-yl-4-methoxybenzene-sulfonate (3l), N-(7-Cyano-3,4-dihydroisoquinolin-2(1H)-yl)-2-ethylbenzamide (4a), N-(6,7-Dimethoxy-3,4-dihydroisoquinolin-2(1H)-yl)-4-ethylbenzamide (4b), 4-Ethyl-N-(1-isopropyl-6,7-dimethoxy-3,4-dihydroisoquinolin-2(1H)-yl)benzamide (4c), N-(7-Cyano-3,4-dihydroisoquinolin-2(1H)-yl)-4-ethylbenzamide (4d), N-(6-Chloro-3,4-dihydroisoquinolin-2(1H)-yl)-4-ethylbenzamide (4e), methyl-2-(4-ethylbenzamido)-6-((4-ethylbenzoyl)oxy)-1,2,3,4-tetrahydroisoquinoline-1-carboxylate (4f), and N-(7-Chloro-3,4-dihydroisoquinolin-2(1H)-yl)-4-ethylbenzamide (Redda-EVK-I-132).

In some embodiments of this aspect of the disclosure, the substituted tetrahydroisoquinoline ethylbenzamide can have the formula:

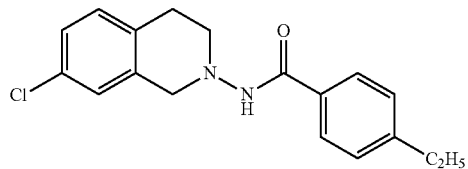

Redda-EVK-I-132

In some embodiments of this aspect of the disclosure, the cell can be a breast cancer cell.

In some embodiments of this aspect of the disclosure, the cell can be a cultured cell or a cell of an animal or human subject.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLES

Example 1

General:

Melting points were determined on a mel-temp 3.0 melting point apparatus and are uncorrected. The structures of the final compounds were confirmed by $^1$HNMR and elemental analysis. The spectra were recorded on Varian Gemini HX 300 MHz spectrometer. All chemical shifts expressed in parts per million (δ, ppm) are reported relative to tetramethylsilane (TMS) as internal standard for solution in CDCl$_3$ as a solvent unless otherwise specified. Elemental analysis of the final compounds were performed by Atlantic Microlab Inc., Norcross, Ga. Flash chromatography was performed on CombiFlash (Teledyne Isco) using RediSep columns. All chemicals and solvents were purchased from Sigma-Aldrich and were used without further purification.

Example 2

General Procedure (Scheme 1, FIG. 2) for the Synthesis of Substituted Tetrahydroisoquinolinium-2,4,6-trimethyl Benzene Sulfonate (11a-11m)

O-mesitylene sulfonyl hydroxylamine (MSH) (10) was used to prepare the N-amino salt as an aminating agent (Tamura et al., (1972) J. Org. Chem. 40: 4133-4135) as previously reported (Gangapuram et al., (2014) J. Cancer Sci. Ther. 6: 161-169). To an ice-cooled solution of substituted isoquinolines (20.67 mmol) in anhydrous methylene chloride and anhydrous methanol (1:1) (60 mL) was added MSH (10) (22.74 mmol) in dry methylene chloride (10 mL) over 5 min with stirring. The reaction was stirred at 0° C. for 6 h at which time ether (80 mL) was added and the suspension filtered. The precipitate was recrystallized from ethyl acetate-methanol (5:1 v/v) to give substituted isoquinolinium 2,4,6-trimethylbenzene-sulfonate salts (11a-11m) in high yields.

Example 3

General Procedure for Acylation Leading to Ylides (12a-12m)

To an ice-cold solution of (11a-11m) (4.16 mmol) in anhydrous tetrahydrofuran (40 mL), containing triethylamine were added substituted acid chlorides (8.34 mmol). The mixture was allowed to proceed for 12 h at 70° C. After the completion of the reaction (monitored by TLC), it was quenched by adding 30 mL of saturated aqueous sodium bicarbonate solution. Extraction with dichloromethane (3 mL×100 mL), drying over anhydrous sodium sulfate and removal of the solvent in vacuo gave the crude product, which was purified on CombiFlash chromatography using ethyl acetate: hexane (3:2 v/v) mixture as eluent. The resultant mono N-acylated ylides were obtained in fair to good yields.

Example 4

General Procedure for Reduction Yielding the Substituted Tetrahydroisoquinolines (2a-2m)

The Ylides (11a-11m) (5 mmol) were dissolved in absolute ethanol (20 mL) and added drop-wise to a solution of sodium borohydride (50 mmol) in absolute ethanol (25 mL) at 0° C. The reactions were allowed to proceed for 5 h to 7 h at the same. Water (35 mL) was added, and allowed to warm up to room temperature. Extraction with dichloromethane (3 mL×50 mL), drying over anhydrous sodium sulfate and removal of the solvent in vacuo gave the desired products. All substituted tetrahydroisoquinolines were purified on CombiFlash using ethyl acetate: dichloromethane (2:3 v/v) as eluent to afford pure compounds (2a-2m) in fair to good yields.

Example 5

N-(7-hydroxy-3,4-dihydroisoquinolin-2(1H)-yl)-4-methoxybenzamide (2d)

Yield 65%, m.p. 192.5° C. to 194.3° C.; $^1$HNMR (CDCl$_3$) δ (ppm): 8.12 (d, J=8.4 Hz, 2H), 3.09 (t, J=5.8 Hz, 2H), 3.42 (t, J=6.0 Hz, 2H), 3.89 (s, 3H), 4.29 (s, 2H), 6.89 (s, 1H), 6.99 (dd, J=2.7, 1.8 Hz, 1H), 7.18 (d, J=9.0 Hz, 1H), 7.21 (s, 1H, —NH, D$_2$O exchange), 7.76 (d, J=8.1 Hz, 2H). Anal. Calcd. for C$_{17}$H$_{18}$N$_2$O$_3$ 0.095 EtOAc: C, 66.57; H, 5.92; N, 9.13. Found: C, 66.93; H, 6.28; N, 8.62.

Example 6

N-(7-hydroxy-3,4-dihydroisoquinolin-2(1H)-yl)-3-methoxybenzamide (2e)

Yield 40%, m.p. 190.5° C. to 192.3° C.; $^1$HNMR (CDCl$_3$) δ (ppm): 7.42-7.51 (m, 3H), 7.14 (d, J=8.0 Hz, 1H), 7.06 (s, 1H, —NH$_2$, D$_2$O exchange), 6.89 (d, J=3.0 Hz, 1H), 6.55 (d, J=9.0 Hz, 2H), 4.21 (s, 2H), 3.82 (s, 3H), 2.84 (t, J=6.0 Hz, 2H), 2.65 (t, J=5.8 Hz, 2H). Anal. Calcd. for C$_{17}$H$_{18}$N$_2$O$_3$ 0.089 EtOAc (306.19): C, 66.69; H, 5.93; N, 9.15. Found: C, 66.58; H, 6.33; N, 8.62.

Example 7

N-(7-hydroxy-3,4-dihydroisoquinolin-2(1H)-yl)-2-methoxybenzamide (2f)

Yield 50%, m.p. 197.3° C. to 199.4° C.; $^1$HNMR (CDCl$_3$) δ (ppm): 2.67 (t, J=5.7 Hz, 2H, C$_4$—H), 2.89 (t, J=6.0 Hz, 2H, C$_3$—H), 3.84 (s, 3H, OCH$_3$ group), 4.21 (s, 2H C$_1$—H), 6.58 (d, J=9.0 Hz, 2H, C$_6$, C$_8$—H), 6.91 (d, J=3.0 Hz, 1H, C$_5$—H), 7.04 (s, 1H, —NH$_2$, D$_2$O exchange), 7.14-7.28 (m, 2H, C$_{3'}$, C$_{5'}$—H), 7.54 (d, J=8.1 Hz, 2H, C$_{4'}$, C$_{6'}$—H). Anal. Calcd. for C$_{17}$H$_{18}$N$_2$O$_3$ 0.095 EtOAc (306.72): C, 66.57; H, 5.92; N, 9.13. Found: C, 66.93; H, 6.28; N, 8.62.

Example 8

2-Ethyl-N-(7-hydroxy-3,4-dihydroisoquinolin-2(1H)-yl) benzamide (2g)

Yield 49%, m.p. 215.3° C. to 215.7° C.; $^1$HNMR (CDCl$_3$) δ (ppm): 7.41 (d, J=8.1 Hz, 2H), 7.23-7.30 (m, 2H), 7.21 (s, 1H, —NH$_2$, D$_2$O exchange), 6.88 (d, J=3.0 Hz, 1H), 6.65 (d, J=3.0 Hz, 1H), 6.48 (d, J=9.0 Hz, 1H), 4.19 (s, 2H), 3.49 (t, J=5.7 Hz, 2H), 3.02 (t, J=6.0 Hz, 2H), 2.78-2.86 (q, J=7.5 Hz, 2H), 1.24 (t, J=7.5 Hz, 3H). Anal. Calcd. for C$_{18}$H$_{20}$N$_2$O$_2$ 0.105 EtOAc: C, 70.74; H, 6.6; N, 9.17. Found: C, 70.51; H, 7.08; N, 8.29.

Example 9

4-Ethyl-N-(6-hydroxy-3,4-dihydroisoquinolin-2(1H)-yl) benzamide (2h)

Yield 55%, m.p. 220.1° C. to 221.6° C.; $^1$HNMR (CDCl$_3$) δ (ppm): 7.62 (d, J=8.1 Hz, 2H), 7.16 (d, J=8.1 Hz, 2H), 7.09 (s, 1H, —NH, D$_2$O exchange), 6.84 (d, J=8.4 Hz, 1H), 6.56 (dd, J=2.7, 5.4 Hz, 1H), 6.43 (d, J=2.1, 1.8 Hz, 1H), 3.92 (s, 2H), 3.18 (t, J=5.7 Hz, 2H), 2.84 (t, J=6.0 Hz, 2H), 2.61-2.72 (q, J=7.5 Hz, 2H), 1.21 (t, J=7.5 Hz, 3H). Anal. Calcd. for C$_{18}$H$_{20}$N$_2$O$_2$ 0.05EtOAc (300.78): C, 71.88; H, 6.70; N, 9.31 Found: C, 72.13; H, 6.79; N, 9.31.

Example 10

4-Ethyl-N-(8-hydroxy-3,4-dihydroisoquinolin-2(1H)-yl) benzamide (2i)

Yield 63%, m.p. 218.5° C. to 220.4° C.; $^1$HNMR (CDCl$_3$) δ (ppm): 7.65 (d, J=8.1 Hz, 2H), 7.17 (d, J=8.1 Hz, 2H), 7.09 (s, 1H, —NH, D$_2$O exchange), 6.79 (d, J=8.4 Hz, 1H), 6.58 (dd, J=2.7, 5.4 Hz, 1H), 6.35 (d, J=2.1, 1.8 Hz, 1H), 3.94 (s, 2H), 3.18 (t, J=5.7 Hz, 2H), 2.86 (t, J=6.0 Hz, 2H), 2.64-2.72 (q, J=7.5 Hz, 2H), 1.18 (t, J=7.5 Hz, 3H). Anal. Calcd. for C$_{18}$H$_{20}$N$_2$O$_2$ (296.36): C, 72.95; H, 6.80; N, 9.45 Found: C, 72.79; H, 6.69; N, 9.28.

Example 11

N,N'-(3,4-dihydroisoquinoline-2,8(1H)-diyl)bis(4-ethylbenzamide) (2j)

Yield 50%, m.p. 113.2° C. to 116.4° C.; $^1$HNMR (CD$_3$OD): δ 7.96 (brs, 1H), 7.81 (d, J=8.1 Hz, 2H), 7.69 (d, J=7.8 Hz, 2H), 7.33 (d, J=7.5 Hz, 1H), 7.25 (d, J=8.1 Hz, 2H), 7.21 (d, J=8.1 Hz, 2H), 7.17 (s, 1H, —NH, D$_2$O exchange), 7.01 (d, J=7.5 Hz, 1H), 4.25 (s, 2H), 3.36 (t, J=6.0 Hz, 2H), 3.07 (t, J=5.1 Hz, 2H), 2.62-2.73 (m, 4H), 1.26 (tt, J=7.5, 7.8 Hz, 6H). Anal. Calcd. for C$_{27}$H$_{29}$N$_3$O$_2$ (427.54): C, 75.85; H, 6.84; N, 9.83. Found: C, 75.59; H, 6.81; N, 9.82.

Example 12

N-(8-amino-3,4-dihydroisoquinolin-2(1H)-yl)-4-ethyl-benzamide (2k)

Yield 45%, m.p. 223.5° C. to 224.8° C.; $^1$HNMR (CD$_3$OD): δ 7.75 (d, J=9.0 Hz, 2H), 7.31 (d, J=8.1 Hz, 2H), 6.93 (t, J=7.8 Hz, 1H), 6.51-6.58 (dd, J=7.5, 4.8 Hz, 2H), 4.18 (s, 2H, —NH$_2$, D$_2$O exchange), 3.91 (s, 2H), 3.15 (t, J=6.0 Hz, 2H), 3.02 (t, J=6.0 Hz, 2H), 2.67-2.74 (q, J=7.8, 7.5 Hz, 2H), 1.25 (t, (t, J=7.8 Hz, 3H). Anal. Calcd. for C$_{18}$H$_{21}$N$_3$O 0.015 EtOAc (296.71): C, 72.89; H, 6.78; N, 13.76 Found: C, 72.87; H, 7.13; N, 14.16.

Example 13

4-Amino-N-(7-bromo-3,4-dihydroisoquinolin-2(1H)-yl) benzamide (2l)

Yield 54%, m.p. 177.8° C. to 179.2° C.; $^1$HNMR (CD$_3$OD): δ 7.59 (d, J=8.7 Hz, 2H), 7.26 (d, J=5.7 Hz, 2H), 7.13 (s, 1H, —NH, D$_2$O exchange), 7.06 (d, J=8.1 Hz, 1H), 6.66 (d, J=9.0 Hz, 2H), 4.03 (s, 2H), 3.15 (t, J=6.0 Hz, 2H), 3.02 (t, J=6.6 Hz, 2H). Anal. Calcd. for C$_{16}$H$_{16}$BrN$_3$O 0.025 EtOAc (348.44): C, 55.49; H, 4.66; N, 12.34 Found: C, 55.15; H, 4.63; N, 12.06.

Example 14

4-(Ethylbenzamido)-1,2,3,4-tetrahydroisoquinolin-7-yl 4-ethylbenzoate (2m)

Yield 60%, m.p. 195.8° C. to 198.2° C.; $^1$HNMR (CD$_3$OD): δ 7.74 (d, J=8.1 Hz, 2H); 8.06 (d, J=8.4 Hz, 2H), 7.42 (s, 2H, —NH D$_2$O exchange), 7.38 (d, J=8.1 Hz, 2H), 7.32 (d, J=8.1 Hz, 2H), 7.23 (d, J=8.1 Hz, 1H), 7.03 (dd, J=2.4, 5.7 Hz, 1H), 6.95 (d, J=5.4 Hz, 1H), 4.13 (s, 2H), 3.23 (t, J=5.4 Hz, 2H), 3.12 (t, J=5.4 Hz, 2H), 2.67-2.79 (m, 4H), 1.26 (tt, J=7.5, 7.8 Hz, 6H). Anal. Calcd. for C$_{27}$H$_{28}$N$_2$O$_3$ (428.52): C, 5.68; H, 6.59; N, 6.54. Found: C, 75.41; H, 6.37; N, 6.52.

Example 15

General Procedure (Scheme 2) Synthesis of Substituted Tetrahydroisoquinolines (THIQs) (3a-3l)

The aminating agent, 2, 4-Dinitrophenyl hydroxylate (13) was prepared following the reported procedure (Legault & Charette (2003) *J. Org. Chem.* 68: 7119-7122) and was used to make the substituted isoquinoline dinitrophenoxy salts. The salts were obtained after adding diethyl ether to the reaction mixture after completion, filtering the resulting suspension to yield yellow solid.

Example 16

General Procedure for the Synthesis of Ylides

Dry THF (10 mL) was added to the substituted isoquinoline dinitrophenoxy salts and the resulting suspension was stirred at ambient temperature for 10 min. Et$_3$N (2 eq) was added to the reaction mixture and stirred well. After 15 min. the substituted acid chlorides/sulfonyl chlorides (1.5 eq) were added and the reaction mixture was stirred at ambient temperature for 3 hrs. Heating the reaction mixture at 70° C. for 1 hr helps in complete conversion in some reactions, but in many instances is not necessary. For isoquinolines having —NH$_2$ or —OH substituents, heating resulted in the formation of major amounts of bis-acylated products, hence avoided. TLC (100% ethyl acetate) revealed the product formation. Reaction mixture was quenched with saturated sodium bicarbonate solution and the compounds extracted with dichloromethane (50 mL), dried over sodium sulfate, filtered and solvent evaporated. The crude compounds were used as such for the next step without further purification.

Example 17

General Procedure for the Synthesis of Substituted Tetrahydroisoquinolines

Absolute ethanol (10 mL) was added to the slides prepared by the above procedure, cooled to 0° C. and stirred for 15 min. Sodium borohydride (8 eq.) was added in one portion to the reaction and stirred further at 0° C. for 3 h to 5 h. TLC with hexane:ethyl acetate (1:1) as eluent showed a new spot corresponding to the product. Reaction was stopped, quenched by addition of water (3 mL), ethanol evaporated, brine (20 mL) was added and extracted using dichloromethane. The organic layer collected, dried over sodium sulfate, filtered and solvent evaporated. The residue thus obtained was subjected to CombiFlash chromatography using 0% to 100% hexane:ethylacetate gradient.

Example 18

4-(tert-butyl)-N-(5-Methoxy-3, 4-dihydroisoquinolin-2(1H)-yl) benzamide (3a)

Yield 82%; m.p. 191° C. to 193° C.; $^1$HNMR (CDCl$_3$) δ (ppm): 7.62 (d, J=8.7 Hz, 2H), 7.37 (d, 8.7 Hz, 1H), 7.09 (s, (br), 1H, NH), 7.07 (t, J=7.8 Hz, 1H), 6.65 (d, J=7.8 Hz, 1H), 6.58 (d, J=7.8 Hz, 1H), 4.09 (s, 2H), 3.75 (s, 3H), 3.271 (t, J=6 Hz, 2H), 2.83 (t, J=6 Hz, 2H), 1.24 (s, 9H). Anal. Calcd. for C$_{21}$H$_{26}$N$_2$O$_2$. 0.15 EtOAc: C, 71.72, H, 7.45, N, 7.97; Found C, 71.95, H, 7.44, N, 7.50.

Example 19

4-(tert-butyl)-N-(5-Hydroxy-3,4-dihydroisoquinolin-2(1H)-yl) benzamide (3b)

Yield 55%; m.p. 233° C.; $^1$HNMR (CDCl$_3$) δ (ppm): 7.76-7.38 (dd, J=6.3, 1.5 Hz, 2H), 7.49-7.46 (m, 2H), 6.89 (m, J=7.5 Hz, 1H), 6.71 (d, J=7.5 Hz, 1H), 6.45 (d, J=7.2 Hz, 1H), 3.93 (s, 2H), 3.036 (t, J=6.3 Hz, 2H), 2.38 (t, J=6 Hz, 2H), 1.34 (s, 9H). Anal. Calcd. for C$_{20}$H$_{24}$N$_2$O$_2$: C, 74.04, H, 7.46, N, 8.64; Found C, 73.92, H, 7.43, N, 8.51.

Example 20

N,N'-(3, 4-Dihydroisoquinoline-2, 5(1H)-diyl)bis(4-ethylbenzamide) (3c)

Yield 5%; m.p. 216° C. to 218° C.; $^1$HNMR (CDCl$_3$) δ (ppm): 7.74 (d, J=8.4 Hz, 2H), 7.65-7.60 (m, 3H), 7.26 (d, J=8.4 Hz), 7.17-7.12 (m, 3H), 6.835 (d, J=7.5 Hz, 1H), 4.09 (s, 2H), 3.23 (t, 2H), 2.82 (t, J=6 Hz, 2H), 2.67-2.57 (m, 4H), 1.22-1.14 (m, 6H).

Example 21

N-(5-Acetamido-3,4-dihydroisoquinolin-2(1H)-yl)-4-ethylbenzamide (3d)

Yield 60%; m.p. 295° C. to 297° C.; $^1$HNMR (CD$_3$OD) δ (ppm): 7.73-7.62 (d, J=8.4 Hz, 2H), 7.33 (d, J=8.1 Hz, 2H), 7.26-7.14 (m, 2H), 7.0 (d, J=6.9 Hz, 1H), 4.10 (s, 2H), 3.19 (t, J=6.3 Hz, 2H), 2.95 (t, J=6 Hz, 2H), 2.7 (q, J=7.8 Hz, 2H), 2.15 (s, 3H), 1.25 (t, J=7.8 Hz, 3H). Calcd. for C$_{20}$H$_{23}$N$_3$O$_2$: C, 71.19, H, 6.87, N, 12.45; Found C, 71.10, H, 6.97, N, 11.53.

Example 22

N-(5-(Benzyloxy)-3,4-dihydroisoquinolin-2(1H)-yl)-4-(tertbutyl) benzamide (3e)

Yield 52%; m.p. 179° C. to 181° C.; $^1$HNMR (CDCl$_3$) δ (ppm): 7.70 (d, J=8.7 Hz, 2H), 7.45-7.29 (m, 7H), 7.12 (t, J=7.8 Hz, 1H), 6.78 (d, J=7.8 Hz, 1H), 6.66 (d, J=7.8 Hz, 1H), 5.08 (s, 2H), 4.18 (s, 2H), 3.33 (t, J=6.3 Hz, 2H), 2.99 (t, J=6.3 Hz, 2H), 1.32 (s, 9H). Anal. Calcd. for C$_{27}$H$_{30}$N$_2$O$_2$: C, 78.23, H, 7.29, N, 6.76; Found C, 78.13, H, 7.20, N, 6.61.

Example 23

4-Ethyl-N-(5-hydroxy-3,4-dihydroisoquinolin-2(1H)-yl) benzamide (3f)

Yield 32%; m.p. 218° C. to 220° C.; $^1$HNMR (CDCl$_3$) δ (ppm): 7.75 (d, J=8.1 Hz, 2H), 7.29-7.25 (m, 2H), 6.92 (t, J=7.5 Hz, 1H), 6.72 (d, J=8.4 Hz, 1H), 6.49 (d, J=7.2 Hz), 4.00 (s, 2H), 3.12 (t, J=5.86 Hz, 2H), 2.74-2.67 (q, J=7.62 Hz, 2H), 3.5 (t, J=6 Hz, 2H), 1.26 (t, J=7.62 Hz, 3H). Anal. Calcd. for C$_{18}$H$_{20}$N$_2$O$_2$. 0.05 EtOAc: C, 71.88, H, 6.70, N, 9.31; Found C, 71.48, H, 6.89, N, 9.06.

Example 24

Methyl-2-(4-ethylbenzamido)-1,2,3,4-tetrahydroisoquinoline 6-carboxylate (3h): Yield 37%; m.p. 137° C. to 139° C.; $^1$HNMR (CDCl$_3$) δ (ppm): 7.86-7.83 (dd, J=6.4, 1.76 Hz, 2H), 7.79-7.76 (dd, J=6.74, 1.76 Hz, 2H), 7.09-6.96 (m, 5H), 6.85-6.80 (m, 2H), 3.91 (s, 3H), 3.89 (s, 3H), 3.86 (s (br), 2H), 2.75 (t, J=6.3 Hz, 2H), 2.60 (t, J=6 Hz, 2H).

Example 25

2-(4-Ethylbenzamido)-1,2,3,4-tetrahydroisoquinoline-6-carboxylic acid (3k)

Yield 18%; m.p. 251° C. to 253° C.; $^1$HNMR (CD$_3$OD) δ (ppm): 7.84-7.76 (m, 4H), 7.34 (d, J=7.8 Hz, 2H, 7.21 (d, J=8.1 Hz, 1H), 4.27 (s, 2H), 3.34-3.30 (m, 2H), 3.17-3.15 (m, 2H), 2.75-2.67 (q, J=7.5 Hz, 2H), 1.25 (t, J=7.5 Hz, 3H).

Example 26

2-(4-Methoxyphenylsulfonamido)-1,2,3,4-tetrahydroisoquinolin-5-yl-4-methoxybenzene-sulfonate (3l)

Yield 27%; m.p. 182° C. to 183° C.; $^1$HNMR (CDCl$_3$) δ (ppm): 7.80-7.77 (m, 2H), 7.69 (d, J=7.8 Hz), 7.380 (s, 1H, NH), 7.24 (m, 2H), 7.067 (d, J=8.7 Hz), 4.22 (s, 2H), 3.89 (s, 3H), 3.31 (t, J=6.0 Hz, 2H), 3.07 (t, J=5.7 Hz, 2H), 2.71-2.63 (q, J=7.8 Hz, 2H), 1.22 (t, J=7.8 Hz, 3H). Anal. Calcd. for C$_{23}$H$_{24}$N$_2$O$_7$S$_2$: C, 54.75, H, 4.79, N, 5.55; Found C, 54.60, H, 4.80, N, 5.35.

Example 27

General Procedure (Scheme 3, FIG. 4) Synthesis of Substituted Tetrahydroisoquinolines (THIQs) (4a-4f)

The respective commercially available starting materials (tetrahydroisoquinolines) were purchased and treated with NaNO$_2$ to obtain tetrahydroquinoline-N-Oxides followed by the reduction using Zn-Acetic acid to obtain the N-Amino tetrahydroisoquinolines. The resulting compounds were used as such for the next reaction without further purification.

Example 28

General Procedure for the Synthesis of Substituted Tetrahydroisoquinolines

To an ice-cooled solution of N-amino tetrahydroisoquinolines (0.5 mmol) in anhydrous tetrahydrofuran (5 mL) containing triethylamine (1.5 mmol) was added substituted acid chlorides (0.76 mmol). The mixture was allowed to proceed for 4 h at room temperature. After completion of the reaction (monitored by TLC), it was quenched by adding 30 mL of saturated aqueous sodium bicarbonate solution. Extraction with dichloromethane (2 mL×35 mL), drying over anhydrous sodium sulfate and removal of the solvent in vacuo gave the crude product, which was purified on Combiflash chromatography using ethyl acetate: hexane (3:2 v/v) as an eluent to yield the desired products.

Example 29

N-(7-Cyano-3,4-dihydroisoquinolin-2(1H)-yl)-2-ethylbenzamide (4a)

Yield 38%; m.p. 162° C. to 167° C.; $^1$HNMR (CDCl$_3$) δ (ppm): 7.45-7.17 (m 6H), 6.97 (s, 1H), 4.19 (s, 2H), 3.35-3.31 (m, 2H), 3.12, t, J=5.4 Hz, 1H), 2.85-2.77 (q, J=7.5 Hz, 2H), 1.25 (t, J=7.5 Hz, 3H).

Example 30

N-(6, 7-Dimethoxy-3, 4-dihydroisoquinolin-2(1H)-yl)-4-ethylbenzamide (4b)

Yield 46%; m.p. 224° C. to 225° C.; $^1$HNMR (CD$_3$OD) δ (ppm): 7.89 (d, J=8.1 Hz, 2H), 7.39 (d, J=8.4 Hz, 2H), 6.85 (s, 1H), 6.89 (s, 1H), 4.71 (s, 2H), 3.89-3.85 (m, 2H), 3.25 (t, J=6.3 Hz, 2H), 2.77-2.69 (q, J=7.5 Hz, 2H), 1.26 (t, J=7.5 Hz, 3H).

Example 31

4-Ethyl-N-(1-isopropyl-6, 7-dimethoxy-3, 4-dihydroisoquinolin-2(1H)-yl)benzamide (4c)

Yield 44%; m.p. 162° C. to 163° C.; $^1$HNMR (CDCl$_3$) δ (ppm): 7.58 (d, 2H, J=8.4 Hz), 7.20 (d, 2H, J=8.1 Hz), 6.16 (m, 2H), 3.86 (s, 3H), 3.84 (s, 3H), 3.69 (d, 1H, J=6.6 Hz), 3.45-3.39 (m, 1H), 3.32-3.26 (m, 1H), 2.82-2.77 (m, 2H), 2.66 (q, 2H, J=7.8 Hz), 1.97-1.91 (m, 1H), 1.27-1.18 (m, 3H), 1.13 (d, 3H, J=6.9 Hz), 0.99 (d, 3H, J=6.6 Hz).

Example 32

N-(7-Cyano-3,4-dihydroisoquinolin-2(1H)-yl)-4-ethylbenzamide (4d)

Yield 28%; Sticky solid; $^1$HNMR (CDCl$_3$) δ (ppm): 7.69 (d, J=8.1 Hz, 2H), 7.44-7.41 (m, 2H), 7.28-7.20, (m, 3H), 4.20 (s, 2H), 3.34-3.31 (m, 2H), 3.09 (t, J=6.0 Hz, 2H), 2.72-2.64 (q, J=7.5 Hz, 2H), 1.23 (t, J=7.8 Hz, 3H).

Example 33

N-(6-Chloro-3,4-dihydroisoquinolin-2(1H)-yl)-4-ethylbenzamide (4e)

Yield 42%; m.p. 205° C. to 206° C.; $^1$HNMR (CDCl$_3$) δ (ppm): 7.68 (d, 2H, 7.5 Hz), 7.25-7.11 (m, 4H), 6.949 (1H, J=8.7 Hz), 4.16 (s, 2H), 3.30 (m, 2H), 3.02 (m, 2H), 2.68 (q, 2H, J=7.5 Hz), 1.23 (t, 3H, J=7.5 Hz).

Example 34

Methyl-2-(4-ethylbenzamido)-6-((4-ethylbenzoyl) oxy)-1,2,3, 4-tetrahydroisoquinoline-1-carboxylate (4f)

Yield 12%; m.p. 150° C. to 152° C.; $^1$HNMR (CDCl$_3$) δ (ppm): 8.14 (m, 3H), 7.71 (d, J=7.8 Hz, 2H), 7.46 (d, J=8.4 Hz, 1H), 7.34-7.25 (m, 3H), 7.04-7.01 (m, 2H), 5.15 (s, 1H), 3.77 (s, 3H), 3.39-3.31 (m, 2H), 2.98-2.93 (m, 2H), 2.78-2.66 (m, 4H), 1.31-1.22 (m, 6H).

Example 35

Antiproliferative Activity Studies

The antiproliferative activities of substituted tetrahydroisoquinolines 2a-2m, 3a-3l and 4a-4f were evaluated according to the procedure reported previously (Crouch et al., (1993) *J. Immunol. Methods* 160: 81-88). The compounds were screened against human ER (+) MCF-7 (breast), ER (−) MDA-MB-231 (breast), and Ishikawa (endometrial) cancer cell lines in comparison to tamoxifen (TAM), Raloxifene (RAL) and 4-hydroxytamoxifen (4-OHT).

Material:

Human MCF-7 and MDA-MB-231 breast cancer cell lines were purchased from the NCI. The human Ishikawa endometrial cancer cell line was purchased from Sigma Aldrich. All three cell lines were cultured in phenol red-free RPMI-1640 (Hyclone) (500 mL) supplemented with L-glutamine-dipeptide (Hyclone) (5 mL), and 10% fetal bovine serum (Atlanta Biologicals) (50 mL).

Method:

The cell lines were cultured and treated with compounds under study including the standard TAM ranging from 0.01 nM to 100,000 nM concentration in the presence of 10 nM estradiol using the previous reported method (Suresh et al., (2014) *Lett. Drug Des. Discov.* 11: 428-436). The results expressed as IC$_{50}$ (inhibitory concentration of 50%) were the averages of three data points for each concentration and were calculated using GraphPad Prism 4.0.

The ER (−) MDA-MB-231 breast cancer cell line constitutes an original model for identifying the ER-independent mechanisms of TAM antiproliferative effects (Colletta et al., (1994) *Breast Cancer Res. Treat.* 31: 5-9; Butta et al. (1992) *Cancer Res.* 52: 4261-4264).

Thus, in the present study the antiproliferative activity of compounds 2-4 against human ER (−) MDA-MB-231 breast cancer cell lines were also investigated to know their mechanism of action. The results showed that compounds 2b, 2i and 3g (IC$_{50}$=0.13 µg/mL, 1.36 µg/mL, 0.23 µg/mL) were more potent than TAM (IC$_{50}$=7.85 µg/mL) shown in Table 1. Furthermore, compound 2i shows reasonable selectivity towards MCF-7 cell lines than MDA-MB-231 (IC$_{50}$=0.61 µg/mL, 1.36 µg/mL respectively), showing that this particular compound may be acting as ER inhibitor. Compounds (2b) and (3g) may also inhibit cell proliferation via ER-independent mechanism in comparison to TAM. Recent work (Gangapuram et al., (2014) *J. Cancer Sci. Ther.* 6: 161-169) indicates that compound (2b) acts as a potent microtubule-destabilizing agent by holding static the microtubule network, thereby preventing mitosis. Cell viability studies on similar compounds, tetrahydropyridines (THPs) indicated that the dosage system used in the experiments could not lead to non-specific high toxicity effect of these compounds against normal cells.

Example 36

Molecular Modeling Studies

Docking Method:

The crystal structures of ERα-4-OHT complex (PDB: 3eRT), ERβ-RAL complex (PDB: QKN) and Tubulin-Taxol complex (PDB: 1JFF) whose coordinates were obtained from RCSB Protein Data Bank were used as a template to dock the active THIQs of present study. The crystal structures were imported into Sybyl-X 1.3 (Khairy et al., (2012) *Chem. Commun.* 48: 10832-10834) modeling suite and using structure preparation tool, Chain A (ERα-4-OHT and ERβ-RAL), Chain B (Tubulin-TA1) were extracted, hydrogen atoms were added, MMFF94s force fields and MMFF94 charges were assigned to the atoms and energy minimized. The 3d structures of the substituted THIQs along with the co-crystallized ligands, 4-Hydroxytamoxifen (OHT), Raloxifene (RAL) and Taxol (TA1) were generated by Sybyl sketch and saved as single molecular file (sdf). The conformer ensembles of all the compounds to be docked were generated using OMEGA v2.4.6, OpenEye Scientific Software (Hawkins et al., (2010) *J. Chem.Inf. Model* 50: 572-584; McGann M. OEDOCKING 3.0.1. OpenEye Scientific Software; Santa Fe, N. Mex.) prior to docking. OMEGA ensures that low strain energy conformations were retained in the ensemble. Since the complexes in the present study have bound ligands (OHT, RAL, TA1 respectively), HYBRID v3.0.1 of OEDocking (Jug et al., (2015) *J. Mol. Model.* 21: 164; McGann M. (2012) *J. Computer-Aided Mol. Des.* 26: 897-906) was chosen as the appropriate docking method for the studies. The dock resolution was set to 'High" to get the best results. The scoring function used in this process to evaluate the poses in HYBRID is HYBRID_Chemgauss4 (McGann et al., (2003) *Biopolymers* 68: 76-90). It uses Gaussian-smoothed potentials to measure the complementary nature of ligand poses within the active site.

Example 37

Docking Studies

The X-ray structure of Ligand Binding Domain (LBD) of estrogen receptors has provided a better way to understand the ER binding site and that of 3 chain of Tubulin-Taxol complex to understand the Taxol binding domain. The validation of the docking poses of the bound ligands (antagonists) in individual crystal structures was done using OEdocking application, HYBRID (McGann et al., (2003) *Biopolymers* 68: 76-9041) after generating the receptors using "Make Receptor version 3.0.1" module in OEdocking. The re-docking of the co-crystallized ligands has been undertaken to make sure that the bound conformations of the ligands (OHT, RAL, TA1) are reproduced by the selected docking method. Best 10 poses were retrieved and were identical with the original poses of the cognate ligands in the crystal structures with root mean square deviation (rmsd) values between them being <2 Ao, a criterion often used for the correct bound structure prediction and validation.

Example 38

The following compounds Table 2) were synthesized using Scheme I shown in FIG. 2: N-(7-Chloro-3,4-dihydroisoquinolin-2(1H)-yl)-4-ethylbenzamide (Redda-EVK-I-132), N-(6-Chloro-3,4-dihydroisoquinolin-2(1H)-yl)-4-ethylbenzamide (4e), N-(7-Cyano-3,4-dihydroisoquinolin-2(1H)-yl)-4-ethylbenzamide (4d), and 4-Ethyl-N-(1-(furan-2-yl)-3,4-dihydroisoquinolin-2(1H)-yl)benzamide (Redda-EVK-I-135)

Figure 5:
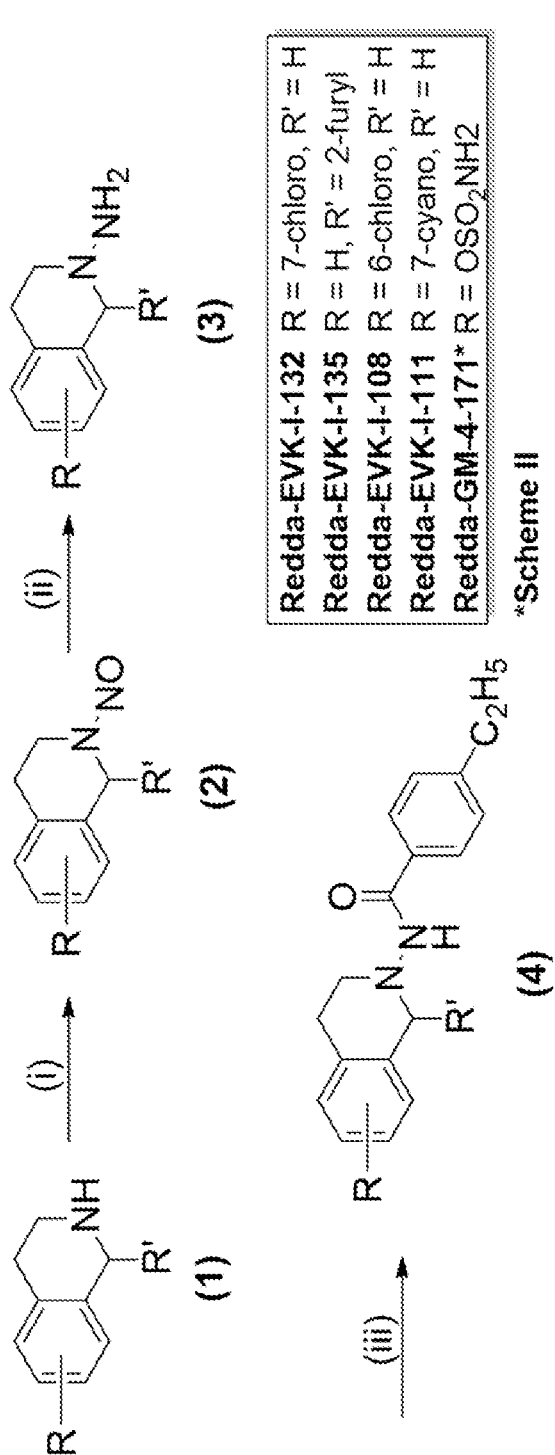
FIG. 5 illustrates a scheme for the synthesis of substituted-2-nitroso-1,2,3,4-tetrahydroisoquinolines (2), substituted-3,4-dihydroisoquinolin-2(1H)-amines (3), and substituted-3,4-dihydroisoquinolin-2(1H-yl)-4-ethylbenzamides (4). Reaction conditions: (i) $NaNO_2$, $CH_3COOH$ $H_2O$, 0° C., (ii) Zn, $CH_3COOH$, (iii) 4-Ethylbenzoyl chloride, $Et_3N$, THF.

Compound 2-(4-Ethylbenzamido)-1,2,3,4-tetrahydroisoquinolin-7-yl-sulfamate (Redda GM-4-171) was synthesized using the scheme shown in FIG. 5.

Example 39

General Procedure (Scheme 1, FIG. 2) for the Synthesis of Substituted-2-nitroso-1,2,3,4 tetrahydroisoquinolines (3)

To ice cold solutions of substituted-1,2,3,4-tetrahydroisoquinolines (1) (1.5 mmol) in a mixture of 2 mL of acetic acid and 2.2 mL of $H_2O$, aqueous solutions of sodium nitrite ($NaNO_2$, 4.5 mmol) in 1.5 mL of $H_2O$ were added drop by drop over 2 min at 0° C. in an ice-water bath. The reaction mixtures were stirred for 3 h.

Thin Layer Chromatography (TLC) indicated that the reactions were complete. The reaction mixtures were extracted with $CH_2Cl_2$ and the organic layers were washed thrice with brine and dried over sodium sulfate. The solvents were evaporated in vacuo to obtain the crude products. Some products were purified at this stage. For example, 7-Chloro-2-nitroso-1,2,3,4-tetrahdyroisoquinoline was column chromatographed (3:1 Hexane:Ethylacetate, gradient elution) using combiflash column chromatography. The desired compound was obtained in moderate yields (62%).

7-Chloro-2-nitroso-1, 2, 3, 4-tetrahydroisoquinoline $^1$HNMR ($CDCl_3$): δ 3.02-3.13 (m, 2H, —$CH_2$), 4.49-4.53 (m, 2H, —$CH_2$), 4.76 (s, 2H, —$CH_2$), 7.13-7.25 (m, 3H, $C_1$'-$C_4$'—H).

Example 40

Synthesis of Substituted-3,4-dihydroisoquinolin-2(1H)-amines (3)

To solution of substituted-2-nitroso-1,2,3,4-tetrahydroisoquinolines (1.01 mmol) in $H_2O$ (3 mL) and acetic acid (3 mL) was slowly added zinc dust in the powder form (0.5 g) at 0° C., keeping the temperature below 10° C. in the process. The reaction mixtures were stirred overnight and then filtered. The filtrates were then treated with 50% aqueous NaOH until they turned slightly basic and then extracted with ethyl acetate, dried over sodium sulfate and concentrated to yield the desired compounds, as sticky solids, which were used without further purification. For example, the 7-Chloro-3,4-dihydroisoquinolin-2(1H)-amine indicated: $^1$HNMR ($CDCl_3$): δ 2.8-2.9 (m, 2H, —$CH_2$), 3.10-3.19 (m, 2H, —$CH_2$), 3.67 (s, 2H, —$CH_2$), 6.93-7.05 (m, 3H, $C_1$'—$C_4$'—H).

Example 41

Synthesis of Substituted-3, 4-dihydroisoquinolin-2(1H-yl)-4-ethylbenzamides (4)

To an ice-cold solution of crude substituted-3,4-dihyroisoquinolin-2(1H)-amines (0.63 mmol) in 5.0 ml of anhydrous tetrahydrofuran, were added 4-ethylbenzoyl chloride (0.945 mmol) and $Et_3N$ (1.89 mmol) with stirring. The reactions were allowed to proceed for 3 h at room temperature. After the reactions are complete (TLC), the reaction mixture was cooled to room temperature and quenched by adding 25 mL of saturated aqueous sodium bicarbonate solution. Extractions with dichloromethane followed by washings with brine (2×10 mL) and concentration of the organic layer in vacuo yielded the desired products, which were further purified by combiflash column chromatography (3:2 Hexane:Ethylacetate gradient elution) resulting in white solids (35-54% yield):

N-(7-Chloro-3, 4-dihydroisoquinolin-2(1H)-yl)-4-ethylbenzamide (Redda-EVK-I-132)

$^1$H NMR (DMSO-d6): δ 1.73 (t, 3H, —$CH_3$, J=7.5 Hz), 2.62 (q, 2H, —$CH_2$, J=7.5 Hz), 2.85-2.95 (m, 2H, —$CH_2$), 3.10-3.20 (m, 2H, —$CH_2$), 4.04 (s, 2H, —$CH_2$), 7.14-7.21 (m, 3H,), 7.30 (d, 2H, J=8.7 Hz), 7.73 (d, 2H, J=8.4 Hz), 9.65 (s, 1H, —NH, deuterium exchangeable using $CDCl_3$ as NMR recording solvent);

4-Ethyl-N-(1-(furan-2-yl)-3, 4-dihydroisoquinolin-2 (1H)-yl)benzamide (Redda-EVK-I-135)

$^1$HNMR ($CDCl_3$): δ 1.22 (t, 3H, —$CH_3$, J=7.8 Hz), 2.68 (q, 2H, —$CH_2$, J=7.5 Hz), 3.51 (m, 1H, —$CH_2$), 3.34 (m, 1H, —$CH_2$), 3.17-3.11 (m, 2H, —$CH_2$), 5.65 (s, 1H, —CH), 6.18 (s, 1H), 6.33 (s, 1H), 6.92-6.90 (d, J=7.2 Hz, 1H), 7.40-7.09 (m, 6H), 7.59 (d, J=7.5 Hz, 2H); N-(6-Chloro-3, 4-dihydroisoquinolin-2(1H)-yl)-4-ethylbenzamide (4e) and N-(7-Cyano-3,4-dihydroisoquinolin-2(1H)-yl)-4-ethylbenzamide (4d) (Eyunni et al., (2017) *J. Cancer Sci. Ther.* 9: 528-540).

Example 42

Synthesis of 2-(4-Ethylbenzamido)-1,2,3,4-tetrahydroisoquinolin-7-yl-sulfamate (GM-4-171)

To a solution of 4-Ethyl-N-(7-hydroxy)-3,4-dihydroisoquinolin-2(1H)-yl)benzamide (7) (0.877 mmol) in dry N,N-dimethyl acetamide (DMA) (5 mL) was added slowly sulfamoyl chloride (1.754 mmol) at 0° C. with stirring and allowed the reaction to come to room temperature. The reaction mixture was stirred at room temperature for 3 h. After the reaction is complete (TLC), the reaction mixture was poured into cold brine solution. Extractions with dichloromethane followed by further washings with brine (2×10 mL) and concentration of the organic layer in vacuo yielded the desired product, which was further purified by combiflash column chromatography (3:2 Hexane:Ethylacetate gradient elution) resulting in a white solid:

$^1$HNMR ($CDCl_3$): δ 1.25 (t, J=7.8 Hz, 3H, —$CH_2$—$CH_3$); 2.71 (q, J=7.8, 7.5 Hz, 2H, —$CH_2$—$CH_3$); 3.05 (s, 1H); 3.10 (t, J=5.4 Hz, 2H); 3.19 (t, J=5.7 Hz, 2H); 4.11 (s, 2H); 5.56 (s, 2H, —$NH_2$, $D_2O$ exchange); 7.04 (d, J=2.4 Hz, 1H); 7.11 (dd, J=2.4, 6.0 Hz, 1H); 7.19 (d, J=8.4 Hz, 1H); 7.31 (d, J=8.1 Hz, 2H); 7.75 (d, J=8.1 Hz, 2H).

Example 43

The compounds Redda-EVK-I-132, Redda-EVK-I-135, and Redda-GM-4-171 were also tested for their cytotoxic effects on human MCF-7 (estrogen receptor positive breast cancer lines), MDA-MB-231 (estrogen receptor negative breast cancer cell lines), and Ishikawa cell lines, using the CELLTITER-GLO® luminescent cell viability assay (Promega, Madison, Wis.) following the manufacturer's instruction.

CELLTITER-GLO® is a homogeneous method based on the quantification of the ATP present, an indicator of metabolically active cells and determining the number of viable cells in culture, which signals the presence of metabolically active cells. Damaged cells are not detected as the ATP leaked from these cells is quickly consumed by ATPases that are also released upon damage. The amount of ATP is determined using a system based on luciferase and D-luciferin resulting in light generation.

The cell lines were plated in 13, 96 well plates at a density of 5000 cells/well in total volumes of 50 μL in phenol-red free medium and incubated for overnight. All compounds were weighed and dissolved in DMSO (10 μM) and tested at different concentrations ranging from 0.01 to 100,000 nM, using Tamoxifen (10 μM) as a positive control. 25 μL of 40 nM estradiol was be added to all appropriate wells on the plate. 25 μL media were added to all wells that did not receive estradiol. 25 μL of stocks (containing the compounds to be tested, DMSO and phenol-red free medium) were added to cells and medium already on plate. 50 µL of medium were added to media wells, and 50 µL of mix (contain 32 mL DMSO+768 mL phenol-red free medium) to all vehicle control wells. Tamoxifen (10 µM) was also added to appropriate wells.

Drug-exposed cells were incubated for 72 h at 37° C. in a 5% $CO_2$ incubator, after which the plates were removed for CELLTITER-GLO® assay and equilibrated at room temperature for 30 min. 100 µL of CELLTITER-GLO® assay reagent was added to each well and cell-lysis was induced on an orbital shaker for 2 min. followed by a further 10 min incubation at room temperature. Luminescence results were read on TriLux Luminometer. The luminescent signal is proportional to the number of active cells present in culture. Dead cells did not affect cell counts because they do not contribute to ATP content. As a consequence, the number of metabolically active cells can be directly derived from the luminescent signal using a specific calibration curve.

Data were expressed as percentage of untreated control (i.e. treatment value-blank/vehicle value-blank), mean+−SE for three replications. The $IC_{50}$ values as shown in Table 1 were determined using GraphPad Prism 4 dose-response curve fitting. These experiments showed that the compounds of the disclosure had value against the target breast cancer cells that were multi-fold less than a currently clinically available anti-breast cancer therapy, Tamoxifen.

Example 44

Molecular Modeling Studies

Figure 6:
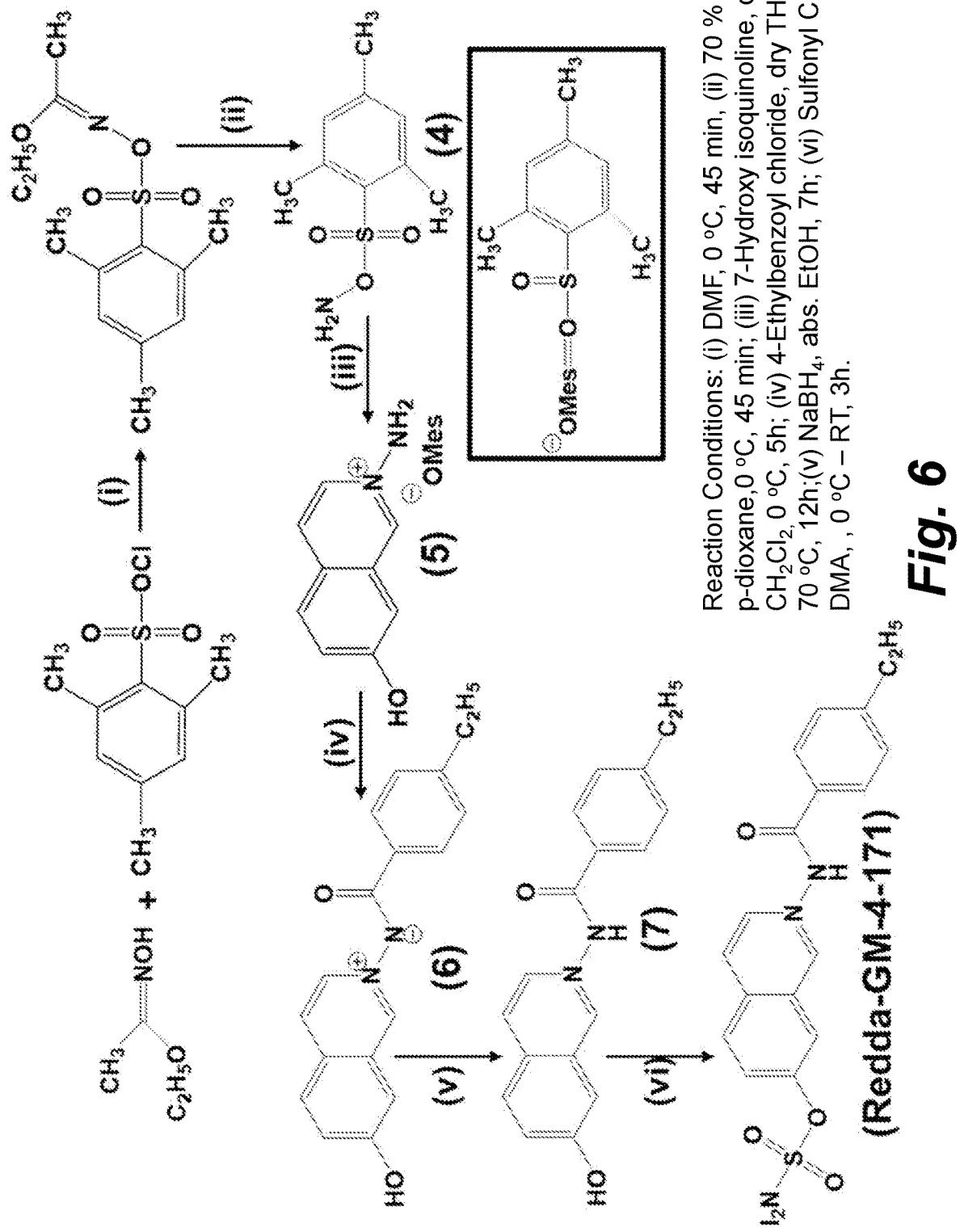
FIG. 6 illustrates a scheme for the synthesis of 2-(4-Ethylbenzamido)-1,2,3,4-tetrahydroisoquinolin-7-yl-sulfamate (GM-4-171). Reaction conditions: (i) DMF, 0° C., 45 min, (ii) 70% $HClO_4$, p-dioxane, 0° C., 45 min, (iii) 7-Hydroxy isoquinoline, dry $CH_2Cl_2$, 0° C., 5h, (iv) 4-ethylbenzoyl chloride, dry THF, 70° C., 12h, (v) $NaBH_4$, abs. EtOH, 7 h; (vi) Sulfonyl Chloride, DMA, 0° C.-RT, 3h.
Figure 7:
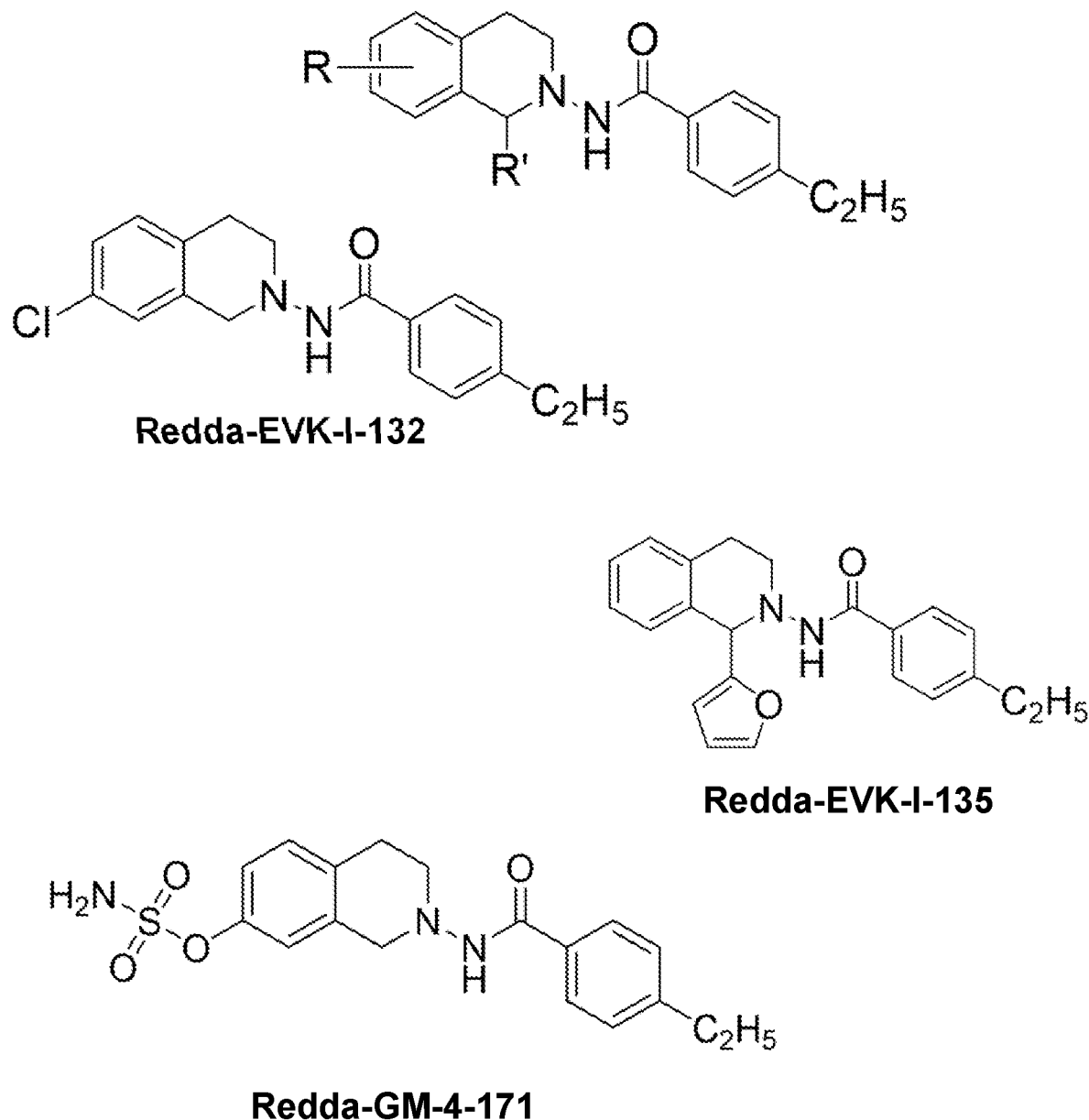
FIG. 7 illustrates the generic structure of the tetrahydroisoquinoline ethylbenzamides (I) and representative substituted variants thereof.
Figure 8:
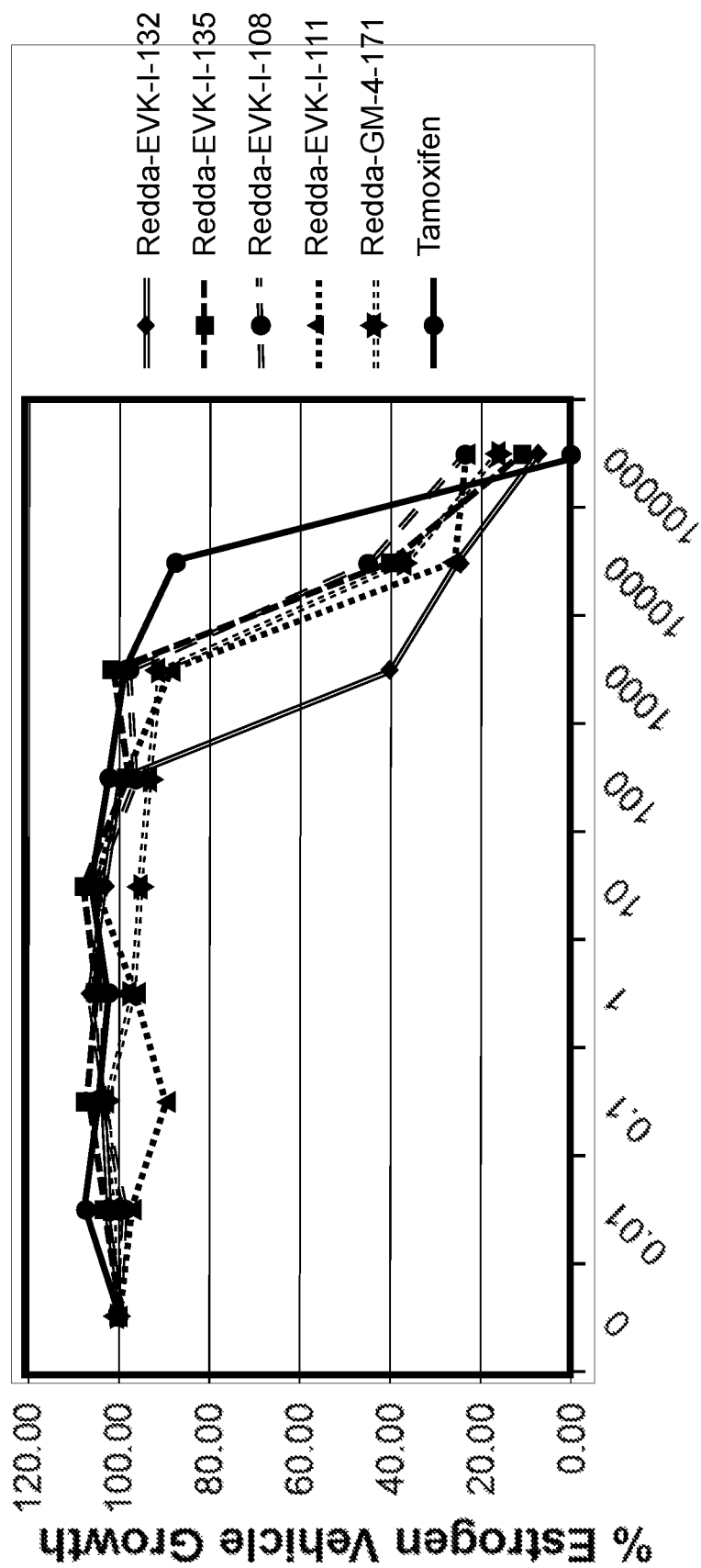
FIG. 8 is a graph illustrating inhibition of the growth of breast cancer MCF-7 cells by representative substituted variants of tetrahydroisoquinoline ethylbenzamide versus tamoxifen.
Figure 9:
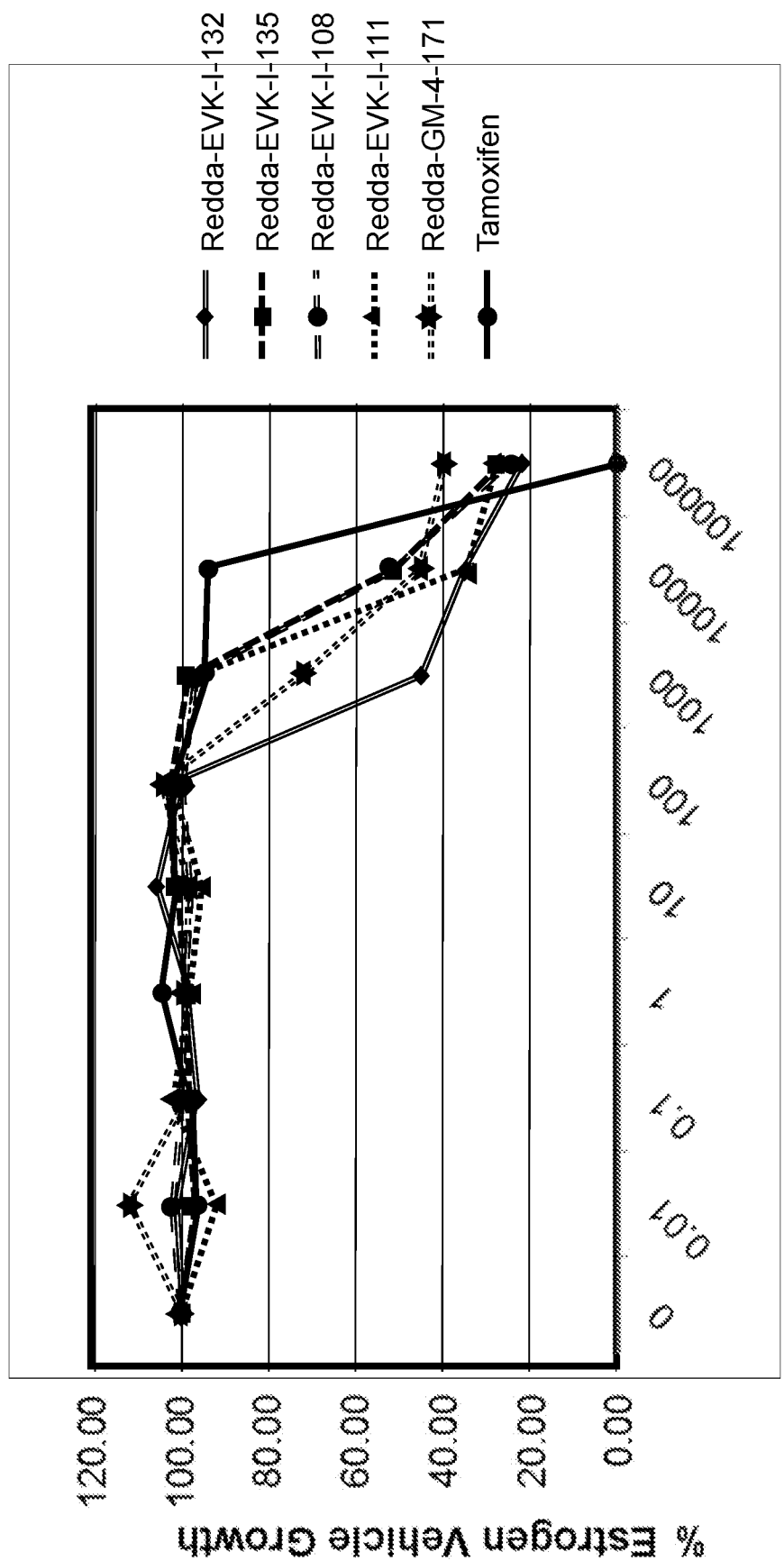
FIG. 9 is a graph illustrating inhibition of the growth of breast cancer MDA-MB-231 cells by representative substituted variants of tetrahydroisoquinoline ethylbenzamide versus tamoxifen
Figure 10:
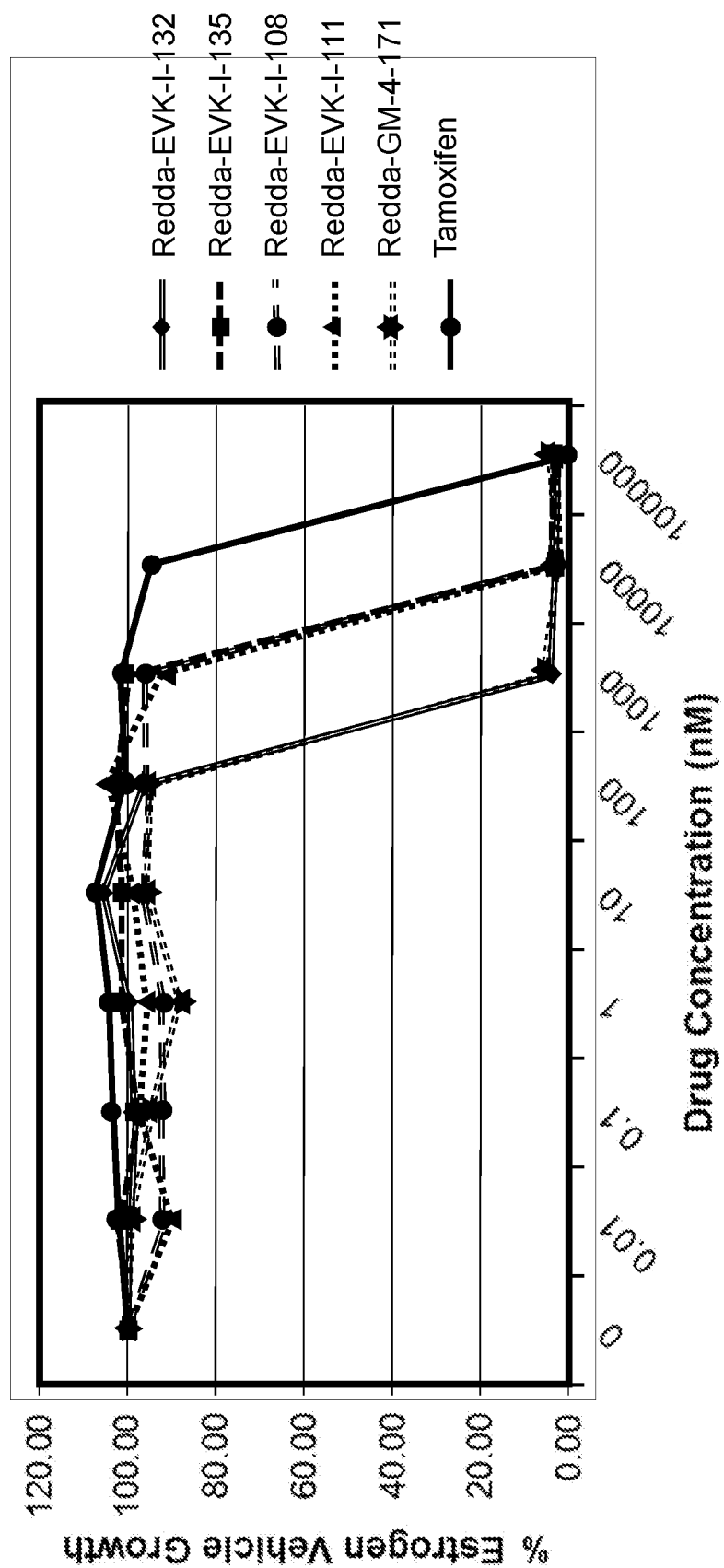
FIG. 10 is a graph illustrating inhibition of the growth of breast cancer Ishikawa cells by representative substituted variants of tetrahydroisoquinoline ethylbenzamide versus tamoxifen.

The top scoring conformations of the THIQs under present study were collected by docking the conformer ensemble (generated by OMEGA (Hawkins et al., (2010) *J. Chem. Inf. Model* 50: 572-584; McGann M. OEDOCKING 3.0.1. *OpenEye Scientific Software*; Santa Fe, N. Mex.) on ERα and ERβ and Tubulin-Taxol receptors (FIGS. 4-6) show the preference for ERα as the ligands fit better in the bigger ligand binding pocket of ERα. These studies also give us an idea of the probable bioactive conformations and binding mode of the newly synthesized ring substituted THIQs which would assist in further optimization studies. The best compound (2b) showed hydrogen bonding interaction with Arg: 394(A) residue in the ERα-4-OHT complex. Similarly a strong hydrogen bonding with THR: 276(B) was observed for this compound in the tubulin-taxol complex. No hydrogen bonds were observed when compound (2b) was docked into the ERβ-RAL complex and the scores were relatively low compared to other molecules in the study. This may be an indication for the selectivity of the compound (2b) and other similar active compounds towards ERα and also its role as a microtubule-destabilizing activity as reported previously (Gangapuram et al., (2014) *J. Cancer Sci. Ther.* 6: 161-169).

What is claimed:

1. A substituted tetrahydroisoquinoline ethylbenzamide having the formula

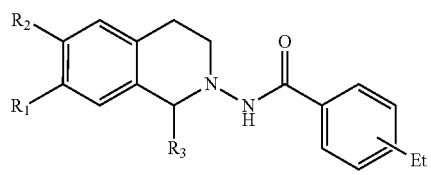

I wherein:
$R_1$ is a hydrogen, a chlorine, a methoxy, cyano, an acyl, a sulfamate, an ethylbenzamide group, an ethylbenzoate group, or an acetamido group;
$R_2$ is a hydrogen, a chlorine, or an hydroxyl group; and
$R_3$ is hydrogen or a furyl group wherein, when $R_3$ is a furyl group $R_1$ and $R_2$ are each a hydrogen.

2. The substituted tetrahydroisoquinoline ethylbenzamide of claim 1, wherein when $R_1$ and $R_3$ are each hydrogen, $R_2$ is a halogen, a cyano, or a sulfamate.

3. The substituted tetrahydroisoquinoline ethylbenzamide of claim 1, wherein $R_2$ is chlorine.

4. The substituted tetrahydroisoquinoline ethylbenzamide of claim 1 selected from the group consisting of 4-Ethyl-N-(6-hydroxy-3,4-dihydroisoquinolin-2(1H)-yl) benzamide (2h), 4-Ethyl-N-(8-hydroxy-3,4-dihydroisoquinolin-2(1H)-yl) benzamide (2i), N,N'-(3,4-dihydroisoquinoline-2,8(1H)-diyl)bis(4-ethylbenzamide) (2j), N-(8-amino-3,4-dihydroisoquinolin-2(1H)-yl)-4-ethylbenzamide (2k), 4-(Ethylbenzamido)-1,2,3,4-tetrahydroisoquinolin-7-yl 4-ethylbenzoate (2m), N,N'-(3,4-Dihydroisoquinoline-2,5(1H)-diyl)bis(4-ethylbenzamide) (3c), N-(5-Acetamido-3,4-dihydroisoquinolin-2(1H)-yl)-4-ethylbenzamide (3d), 4-Ethyl-N-(5-hydroxy-3,4-dihydroisoquinolin-2(1H)-yl) benzamide (3f), methyl-2-(4-ethylbenzamido)-1,2,3,4-tetrahydroisoquinoline-6-carboxylate (3h), 2-(4-Ethylbenzamido)-1,2,3,4-tetrahydroisoquinoline-6-carboxylic acid (3k), N-(7-Cyano-3,4-dihydroisoquinolin-2(1H)-yl)-2-ethylbenzamide (4a), N-(6,7-Dimethoxy-3,4-dihydroisoquinolin-2(1H)-yl)-4-ethylbenzamide (4b), 4-Ethyl-N-(1-isopropyl-6,7-dimethoxy-3,4-dihydroisoquinolin-2(1H)-yl)benzamide (4c), N-(7-Cyano-3,4-dihydroisoquinolin-2(1H)-yl)-4-ethylbenzamide (4d), N-(6-Chloro-3,4-dihydroisoquinolin-2(1H)-yl)-4-ethylbenzamide (4e), methyl-2-(4-ethylbenzamido)-6-((4-ethylbenzoyl)oxy)-1,2,3,4-tetrahydroisoquinoline-1-carboxylate (4f), and N-(7-Chloro-3,4-dihydroisoquinolin-2(1H)-yl)-4-ethylbenzamide (Redda-EVK-I-132).

5. The substituted tetrahydroisoquinoline ethylbenzamide of claim 1, wherein the compound is selected from the group consisting of:

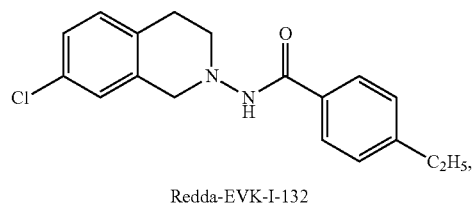 [SMILES: CCc1ccc(C(=O)NN2CCc3ccc(Cl)cc3C2)cc1]

Redda-EVK-I-132

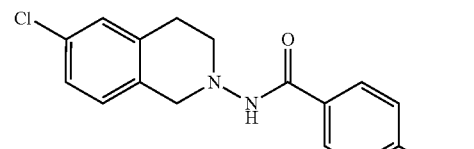

4e

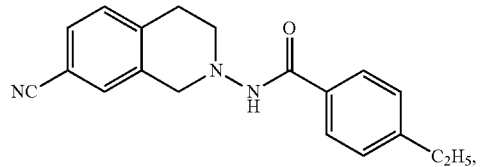

4d

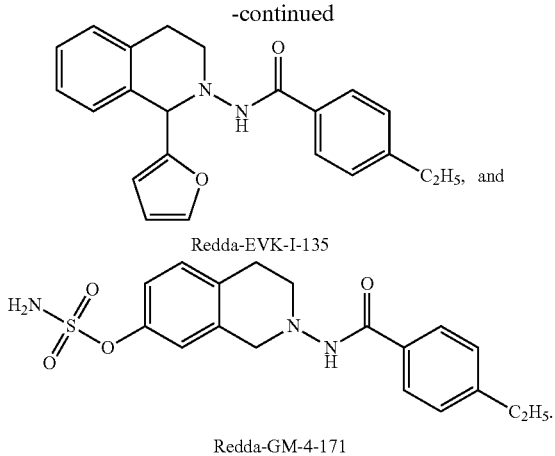

Redda-EVK-I-135

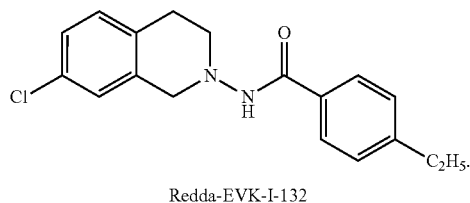 [SMILES: CCc1ccc(C(=O)NN2CCc3ccc(Cl)cc3C2)cc1]

Redda-GM-4-171

6. The substituted tetrahydroisoquinoline ethylbenzamide of claim 1, wherein the compound has the formula:

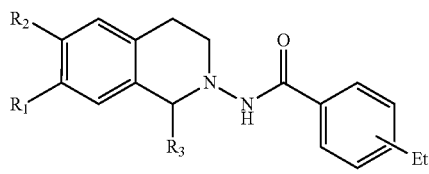

Redda-EVK-I-132

7. A pharmaceutically acceptable composition comprising a substituted tetrahydroisoquinoline ethylbenzamide having the formula I:

I wherein:
- $R_1$ is a hydrogen, a chlorine, a methoxy, cyano, an acyl, a sulfamate, an ethylbenzamide group, an ethylbenzoate group, or an acetamido group;
- $R_2$ is a hydrogen, a chlorine, or an hydroxyl group;
- $R_3$ is hydrogen or a furyl group, wherein when $R_3$ is a furyl group, $R_1$ and $R_2$ are each a hydrogen; and
- a pharmaceutically acceptable carrier.

8. The pharmaceutically acceptable composition of claim 7, wherein when $R_1$ and $R_3$ are each hydrogen, $R_2$ is a halogen, a cyano, or a sulfamate.

9. The pharmaceutically acceptable composition of claim 8, wherein $R_2$ is chlorine.

10. The pharmaceutically acceptable composition of claim 7, wherein the substituted tetrahydroisoquinoline ethylbenzamide is selected from the group consisting of 4-Ethyl-N-(6-hydroxy-3,4-dihydroisoquinolin-2(1H)-yl) benzamide (2h), 4-Ethyl-N-(8-hydroxy-3,4-dihydroisoquinolin-2(1H)-yl) benzamide (2i), N,N'-(3,4-dihydroisoquinoline-2,8(1H)-diyl)bis(4-ethylbenzamide) (2j), N-(8-amino-3,4-dihydroisoquinolin-2(1H)-yl)-4-ethylbenzamide (2k), (Ethylbenzamido)-1,2,3,4-tetrahydroisoquinolin-7-yl 4-ethylbenzoate (2m), N,N'-(3,4-Dihydroisoquinoline-2,5(1H)-diyl)bis(4-ethylbenzamide) (3c), N-(5-Acetamido-3,4-dihydroisoquinolin-2(1H)-yl)-4-ethylbenzamide (3d), 4-Ethyl-N-(5-hydroxy-3,4-dihydroisoquinolin-2(1H)-yl) benzamide (3f), methyl-2-(4-ethylbenzamido)-1,2,3,4-tetrahydroisoquinoline-6-carboxylate (3h), 2-(4-Ethylbenzamido)-1,2,3,4-tetrahydroisoquinoline-6-carboxylic acid (3k), N-(7-Cyano-3,4-dihydroisoquinolin-2(1H)-yl)-2-ethylbenzamide (4a), N-(6,7-Dimethoxy-3,4-dihydroisoquinolin-2(1H)-yl)-4-ethylbenzamide (4b), 4-Ethyl-N-(1-isopropyl-6,7-dimethoxy-3,4-dihydroisoquinolin-2(1H)-yl)benzamide (4c), N-(7-Cyano-3,4-dihydroisoquinolin-2(1H)-yl)-4-ethylbenzamide (4d), N-(6-Chloro-3,4-dihydroisoquinolin-2(1H)-yl)-4-ethylbenzamide (4e), methyl-2-(4-ethylbenzamido)-6-((4-ethylbenzoyl)oxy)-1,2,3,4-tetrahydroisoquinoline-1-carboxylate (4f), and N-(7-Chloro-3,4-dihydroisoquinolin-2(1H)-yl)-4-ethylbenzamide (Redda-EVK-I-132).

11. The pharmaceutically acceptable composition of claim 7, wherein the substituted tetrahydroisoquinoline ethylbenzamide is selected from the group consisting of:

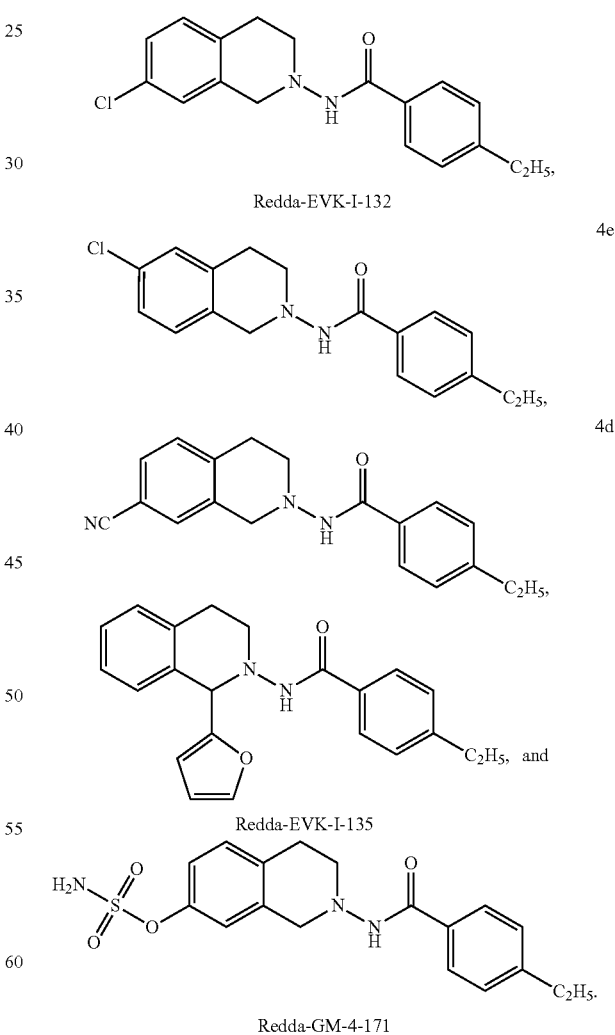

12. The pharmaceutically acceptable composition of claim 7, wherein the substituted tetrahydroisoquinoline ethylbenzamide has the formula:

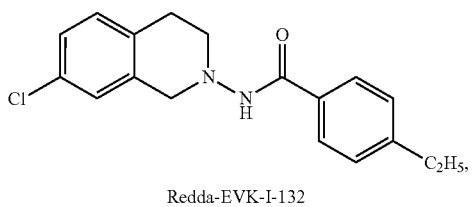 [SMILES: CCc1ccc(C(=O)NN2CCc3ccc(Cl)cc3C2)cc1]

Redda-EVK-I-132

13. The pharmaceutically acceptable composition according to claim 7, wherein said pharmaceutically acceptable composition is formulated to provide an amount of the substituted tetrahydroisoquinoline ethylbenzamide effective in inhibiting the proliferation of a cancer cell cultured in vitro.

14. The pharmaceutically acceptable composition according to claim 13, wherein the cell is a breast cancer cell.

15. The pharmaceutically acceptable composition according to claim 7, wherein said pharmaceutically acceptable composition is formulated to provide a therapeutically effective amount of the substituted tetrahydroisoquinoline ethylbenzamide for inhibiting the proliferation of a cell in vivo.

16. The pharmaceutically acceptable composition according to claim 15, wherein the cell is a cancer cell.

17. The pharmaceutically acceptable composition according to claim 16, wherein the cell is a breast cancer cell.

18. A method of inhibiting the proliferation of a cell comprising contacting a cell with an effective amount of a substituted tetrahydroisoquinoline ethylbenzamide having the formula I:

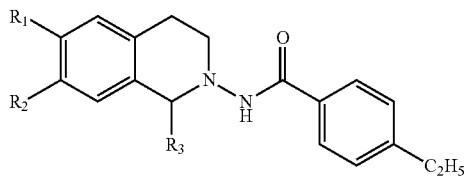

wherein:
- $R_1$ is a hydrogen, a chlorine, a methoxy, cyano, an acyl, a sulfamate, an ethylbenzamide group, an ethylbenzoate group, or an acetamido group;
- $R_2$ is a hydrogen, a chlorine, or an hydroxyl group; and
- $R_3$ is hydrogen or a furyl group, wherein when $R_3$ is a furyl group, $R_1$ and $R_2$ are each a hydrogen; and a pharmaceutically acceptable carrier, thereby reducing the proliferation rate of the cell compared to the proliferation rate of a cell not in contact with the compound.

19. The method of claim 18, wherein the substituted tetrahydroisoquinoline ethylbenzamide is selected from the group consisting of 4-Ethyl-N-(6-hydroxy-3,4-dihydroisoquinolin-2(1H)-yl) benzamide (2h), 4-Ethyl-N-(8-hydroxy-3,4-dihydroisoquinolin-2(1H)-yl) benzamide (2i), N,N'-(3,4-dihydroisoquinoline-2,8(1H)-diyl)bis(4-ethylbenzamide) (2j), N-(8-amino-3,4-dihydroisoquinolin-2(1H)-yl)-4-ethylbenzamide (2k), (Ethylbenzamido)-1,2,3,4-tetrahydroisoquinolin-7-yl 4-ethylbenzoate (2m), N,N'-(3,4-Dihydroisoquinoline-2,5(1H)-diyl)bis(4-ethylbenzamide) (3c), N-(5-Acetamido-3,4-dihydroisoquinolin-2(1H)-yl)-4-ethylbenzamide (3d), 4-Ethyl-N-(5-hydroxy-3,4-dihydroisoquinolin-2(1H)-yl) benzamide (3f), methyl-2-(4-ethylbenzamido)-1,2,3,4-tetrahydroisoquinoline-6-carboxylate (3h), 2-(4-Ethylbenzamido)-1,2,3,4-tetrahydroisoquinoline-6-carboxylic acid (3k), N-(7-Cyano-3,4-dihydroisoquinolin-2(1H)-yl)-2-ethylbenzamide (4a), N-(6,7-Dimethoxy-3,4-dihydroisoquinolin-2(1H)-yl)-4-ethylbenzamide (4b), 4-Ethyl-N-(1-isopropyl-6,7-dimethoxy-3,4-dihydroisoquinolin-2(1H)-yl) benzamide (4c), N-(7-Cyano-3,4-dihydroisoquinolin-2(1H)-yl)-4-ethylbenzamide (4d), N-(6-Chloro-3,4-dihydroisoquinolin-2(1H)-yl)-4-ethylbenzamide (4e), methyl-2-(4-ethylbenzamido)-6-((4-ethylbenzoyl)oxy)-1,2,3,4-tetrahydroisoquinoline-1-carboxylate (4f), and N-(7-Chloro-3,4-dihydroisoquinolin-2(1H)-yl)-4-ethylbenzamide (Redda-EVK-I-132).

20. The method of claim 19, wherein the substituted tetrahydroisoquinoline ethylbenzamide has the formula:

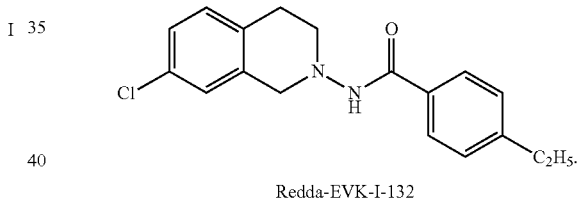

Redda-EVK-I-132

21. The method of claim 19, wherein the cell is a cancer cell.

22. The method of claim 21, wherein the cell is a breast cancer cell.

23. The method of claim 19, wherein the cell is a cultured cell or a cell of an animal or human subject.

* * * * *